US008414883B2

(12) United States Patent
Rommelaere et al.

(10) Patent No.: US 8,414,883 B2
(45) Date of Patent: Apr. 9, 2013

(54) PARVOVIRUS CANCER THERAPY AND COMBINATION WITH CHEMOTHERAPY

(75) Inventors: Jean Rommelaere, Heidelberg (DE); Zahari Raykov, Heidelberg (DE); Joerg Schlehofer, Leimen (DE); Irina Kiprijanova, Heidelberg (DE); Tanja Heimberger, Würzburg (DE); Assia Angelova, Sofia (BG); Karsten Geletneky, Heidelberg (DE); Marc Aprahamian, Heidelberg (DE)

(73) Assignees: Deutsches Krebsforschungszentrum, Heidelberg (DE); Ruprecht-Karls-Universitaet Heidelberg, Heidelberg (DE)

( * ) Notice: Subject to any disclaimer, the term of this patent is extended or adjusted under 35 U.S.C. 154(b) by 0 days.

(21) Appl. No.: 12/810,457

(22) PCT Filed: Dec. 23, 2008

(86) PCT No.: PCT/EP2008/011075
§ 371 (c)(1),
(2), (4) Date: Sep. 24, 2010

(87) PCT Pub. No.: WO2009/083232
PCT Pub. Date: Jul. 9, 2009

(65) Prior Publication Data
US 2011/0020287 A1    Jan. 27, 2011

(30) Foreign Application Priority Data
Dec. 28, 2007    (EP) .................................... 07025216

(51) Int. Cl.
*A61K 48/00* (2006.01)
*A61K 35/76* (2006.01)
*A61P 1/18* (2006.01)

(52) U.S. Cl. .................................... 424/93.2; 435/235.1

(58) Field of Classification Search ........................ None
See application file for complete search history.

(56) References Cited

U.S. PATENT DOCUMENTS

| 6,384,019 | B1 * | 5/2002 | Myhren et al. ................... 514/49 |
| 6,743,423 | B1 | 6/2004 | Knebel-Doeberitz et al. |
| 7,179,456 | B2 * | 2/2007 | Rommelaere et al. ........ 424/93.1 |
| 8,052,968 | B2 * | 11/2011 | Chen et al. .................. 424/93.21 |
| 2001/0044420 | A1 | 11/2001 | Nielsen et al. |
| 2002/0002162 | A1 | 1/2002 | Lee |
| 2004/0072760 | A1 | 4/2004 | Carboni et al. |
| 2004/0220124 | A1 | 11/2004 | Rommelaere et al. |
| 2005/0171036 | A1 | 8/2005 | Arakawa et al. |

FOREIGN PATENT DOCUMENTS

| DE | 198 25 620 A1 | 12/1999 |
| EP | 1 498 127 A1 | 1/2005 |
| JP | 2003-528864 A | 9/2003 |
| JP | 2006-503867 A | 2/2006 |
| WO | WO 01/30366 A2 | 5/2001 |
| WO | WO 01/72721 A2 | 10/2001 |
| WO | WO 03/080077 A1 | 10/2003 |
| WO | WO 2004/030627 A2 | 4/2004 |

OTHER PUBLICATIONS

Wikipedia for Parvovirus, Published on Apr. 5, 2012.*
P. Klein-Bauernschmitt, et al., "Improved Efficacy of Chemotherapy by Parvovirus-mediated Sensitisation of Human Tumour Cells", European Journal of Cancer, Sep. 1, 1996, pp. 1774-1780, vol. 32A, No. 10, XP000867207.
Ulrich-Peter Rohr, et al., "Non-small lung cancer cells are prime targets for p53 gene transfer mediated by a recombinant adeno-associated virus type-2 vector", Cancer Gene Therapy, Dec. 1, 2003, pp. 898-906, vol. 10, XP003000392.
Matthias H.M. Schwarzbach, et al., "Sensitization of sarcoma cells to doxorubicin treatment by concomitant wild-type adeno-associated virus type 2 (AAV-2) infection", International Journal of Oncology, Jun. 1, 2002, pp. 1211-1218, vol. 20, No. 6, XP009100878.
Matteo Di Piazza, et al., "Cytosolic Activation of Cathepsins Mediates Parvovirus H-1-Induced Killing of Cisplatin and TRAIL-Resistant Glioma Cells", Journal of Virology, Apr. 2007, pp. 4186-4198, vol. 81, No. 8, XP002483096.
Valerie Duverger, et al., "Enhancement of Cisplatin-Induced Apoptosis by Infection with Adeno-Associated Virus Type 2", International Journal of Cancer, Feb. 10, 2002, pp. 706-712, vol. 97, No. 5, XP002483144.
Sven Christian Eisold, et al., "Enhanced Sensitivity of Pancreatic Tumour Cells to 5-Fu-Chemotherapy Mediated by Adeno-Associated Virus Type 2 (AAv-2) Infection in Vitro and in Vivo", Gastroenterology, pp. AGA-A531, vol. 118, No. 4, XP000992794, published on Apr. 2000.
Sven Eisold, et al., "Induction of an Antitumoral Immune Response by Wild-Type Adeno-Associated Virus Type 2 in an In Vivo Model of Pancreatic Carcinoma", Pancreas, Jul. 1, 2007, pp. 63-72, vol. 35, No. 1, XP009100879.
International Search Report dated May 20, 2009 (Four (4) pages).
Assia Angelova et al., "Antitumour Effects of Combined Radio- and Parvovirotherapy in N-Ras-Positive Tumour Cells", Acad. Bulg. Sci., 2007, Tome 60, No. 8 (Five (5) pages).

* cited by examiner

*Primary Examiner* — Bao Li
(74) *Attorney, Agent, or Firm* — Crowell & Moring LLP

(57) ABSTRACT

Described is a pharmaceutical composition containing (a) a parvovirus and (b) a chemotherapeutic agent, preferably as separate entities. The parvovirus might be based on parvovirus H1, LuIII, Mouse minute virus (MMV), Mouse parvovirus (MPV), Rat minute virus (RMV), Rat parvovirus (RPV), Rat virus (RV), vectors based on the foregoing viral species, and/or cells capable of actively producing the foregoing viral species. The pharmaceutical composition is beneficial for the treatment of a tumor. Tumors for which a parvovirus or the adjunction of the invention has particular utility include glioma, medulloblastoma, meningioma and pancreatic cancer. Preferred chemotherapeutic agents are gemcitabine and Temozolodine.

8 Claims, 17 Drawing Sheets

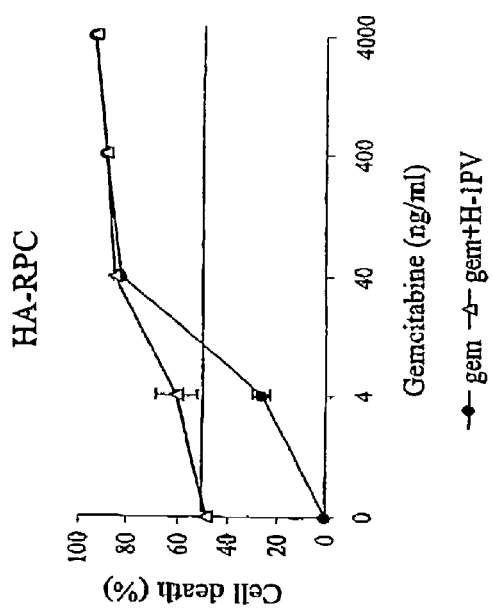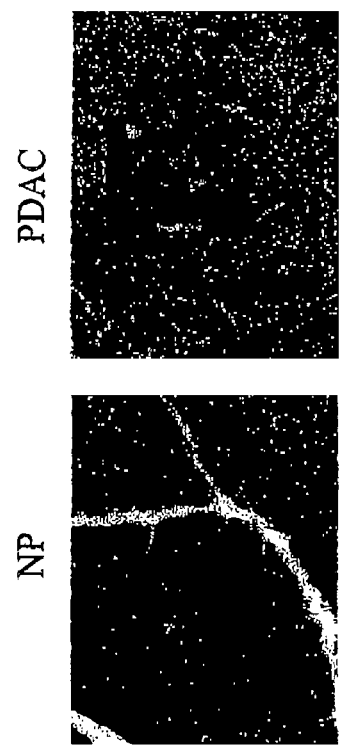
Fig. 3 (a) (b)

PARVOVIRUS CANCER THERAPY AND COMBINATION WITH CHEMOTHERAPY

This application is a national stage of PCT International Application No. PCT/EP2008/011075, filed Dec. 23, 2008, which claims priority under 35 U.S.C. §119 to European Application No. 07025216.8, filed Dec. 28, 2007, the entire disclosure of which is herein expressly incorporated by reference.

The instant application contains a Sequence Listing which has been submitted via EFS-Web and is hereby incorporated by reference in its entirety.

The present invention relates to a pharmaceutical composition comprising (a) a parvovirus and (b) a chemotherapeutic agent and the use of said composition for treatment of cancer, e.g., a brain tumor or pancreatic cancer.

Pancreatic ductal adenocarcinoma (PDAC) is one of the most lethal gastrointestinal malignancies. PDAC is the fourth most frequent cause of cancer-related deaths in North America, the sixth in Europe, and the fifth in the UK.[1,2] The disease is highly resistant to currently available treatments. Surgical resection provides the best possibility for long-term survival, but is feasible in a minority of patients only and is not without risk.[3] In advanced disease where surgery is not an option, chemotherapy comes into play, using in particular gemcitabine or 5-FU (5-fluorouracil), although the effects are still modest and always accompanied by high general toxicity.[4] gemcitabine has been approved by the FDA as a first line therapy for patients with locally advanced or metastatic pancreatic cancer. This drug is a cell-cycle dependent deoxycytidine analogue of the antimetabolite class, that is transported into cells through human equilibrative nucleoside transporters (hENT), and is phosphorylated to its active triphosphate form by deoxycitidine kinase (dCK). An important concern of gemcitabine therapy lies in the development of resistance towards this chemotherapeutic. This resistance can be due to reduced import/phosphorylation of the drug, and/or enhanced export from the cell by means of the ABC transporters family members MDR and MRP1/2, resulting in the depletion of the intracellular pool of activated gemcitabine.[5] Combinations of gemcitabine with other therapeutic regimens are explored to either improve the anticancer effect by eradicating resistant variants or to allow for reduction of the doses of chemotherapy and its ensuing toxicity.

Cancer therapy using viruses or armed vector derivatives that specifically kill neoplastically transformed cells (oncolysis) is a novel approach to the treatment of this lethal disease.[6] Some autonomous parvoviruses belong to the category of so called oncolytic viruses.[7] Parvoviruses are small (25-30 nm) non-enveloped particles containing a 5.1 kb single-stranded DNA genome from which two nonstructural (NS1, NS2) and two capsid (VP1, VP2) proteins are expressed.[8] Parvovirus H-1PV has the unique advantage of triggering a distinct death process, at least in brain and some other tumors, namely the cytosolic relocation and activation of lysosomal proteases (cathepsins).[12] Several members of the parvovirus genus (H-1PV, MVM, LuIII), whose natural hosts are rodents, are presently under consideration for cancer gene therapy applications due to their failure to transform host cells, capacity for asymptomatic infection of humans, and ability to preferentially propagate in (oncotropism) and kill (oncolysis) neoplastically transformed cells.[9,10] MVMp and H-1PV viruses have been shown to exert oncosuppressive activities in vivo, i.e. they are able to inhibit the formation of spontaneous, chemically or virally induced tumors in laboratory animals. Vectors based on a parvoviral expression cassette retain the oncotropic features of the wild type viruses.[11] Despite the impressive results achieved the anticancer efficacy of the most promising parvovirus candidates for human clinical applications (including H-1PV) needs to be improved, e.g., as regards the extension of life span after diagnosis.

Therefore, it is the object of the present invention to provide means for an improved parvovirus-based therapy.

According to the invention this is achieved by the subject matters defined in the claims. The present invention is based on the applicant's findings that by the combined treatment with a parvovirus and a chemotherapeutic agent like gemcitabine (being the most potent chemotherapeutic available for pancreatic cancer and other types of cancer up to date but having still a high toxicity profile) the toxicity of this drug could be reduced and the therapeutic efficiency improved. Pancreatic tumors were implanted orthotopically in Lewis rats and treated with gemcitabine, H-1PV, or both combined in different therapeutic regimens. Tumor size was monitored by computer tomography, while bone marrow, liver and kidney functions were controlled through the levels of clinically relevant markers. Human pancreatic cell lines and their gemcitabine resistant derivatives were tested in vitro for sensitivity to H-1PV or the respective combination with the drug. It could be shown that gemcitabine followed by H-1PV intratumoral injection led to tumor growth retardation, absence of metastases on CT-scan and prolonged survival of the animals. Toxicological screening showed that H-1PV did not cause any additional organ damage, upon combination with gemcitabine. In vitro studies proved that despite the negative effect of gemcitabine on parvovirus replication the combination synergistically summed up the effect of each treatment. Resistant cells remained sensitive to H-1PV killing and could sustain viral expression in the presence of gemcitabine. Comparable results were obtained with the treatment of gliomas using a combination of parvovirus and the chemotherapeutic drug Temozolomide. Thus, parvoviruses have tremendous therapeutic potential to treat cancers like PDAC and gliomas, preferably in combination with chemotherapy in a two step protocol.

(B) Killing of above-mentioned cells treated with increasing concentrations of gemcitabine followed 24 hours later by H-1PV infection at a MOI of 10 cfu/cell. Cell survival was measured through MTT assays performed 72 h after infection in comparison with mock-treated cultures (100%) and inversely expressed as cell death.

Average values and SD bars from 3 independent experiments carried out in triplicates are indicated.

Figure 2:
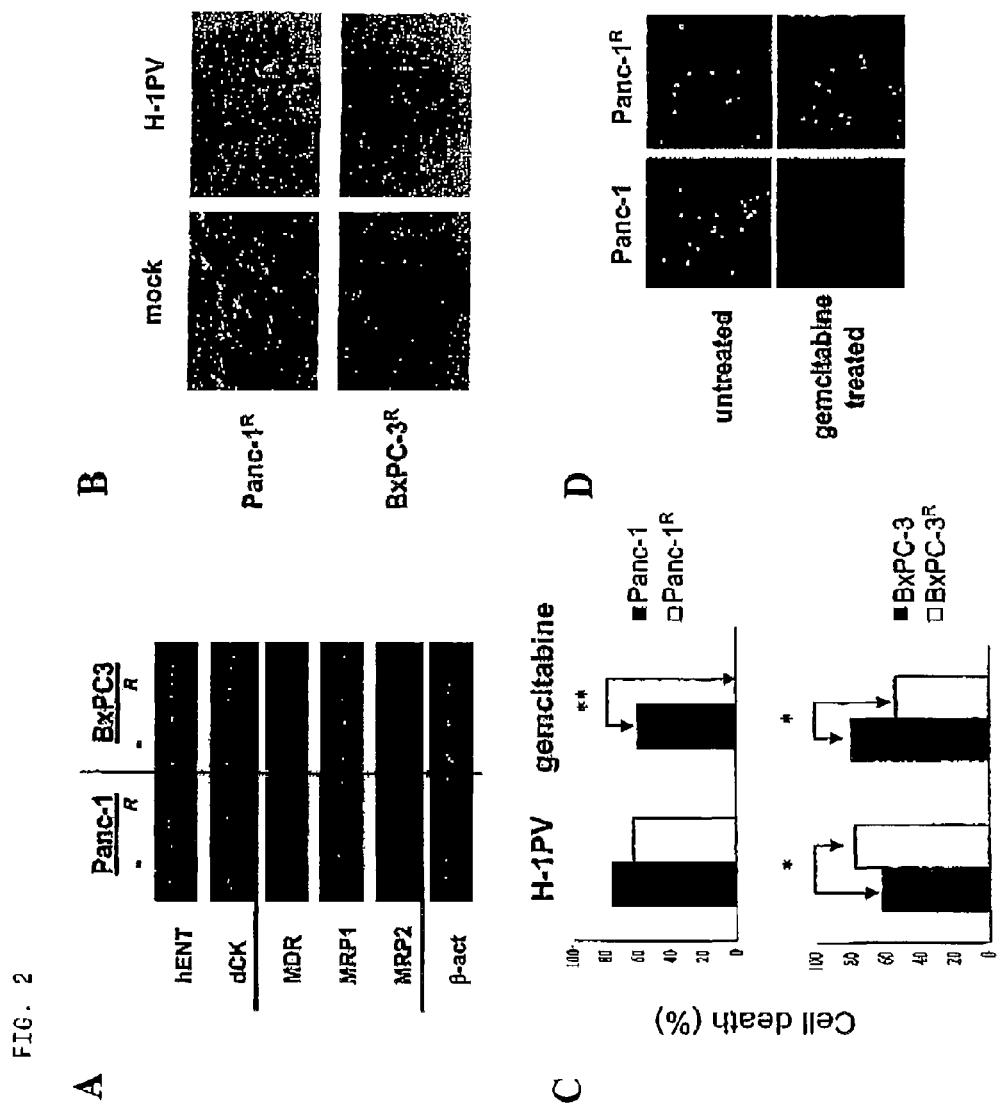

FIG. 2: Characterization of Gemcitabine-Resistant Cell Lines and Their Sensitivity to H-1PV A, Expression of drug resistance markers in parental (−) and gemcitabine-resistant ($^R$) Panc-1 and BxPC-3 cells, as measured by RT-PCR. β-actin transcript levels served as a reference.

B, Micrographs of gemcitabine-resistant ($^R$) Panc-1 and BxPC-3 cells, infected (H-1PV) or not (mock) with H-1PV at MOI=10 RU/cell (magnification 40×).

C, Sensitivity of gemcitabine-resistant ($^R$) and parental Panc-1 (upper part) and BxPC-3 (lower part) cells to H-1PV vs. gemcitabine treatment. Cells were seeded at a density of $2\times10^3$ cells/well in 96-well plates and treated either with H-1PV (10 RU/cell, H-1PV columns) or with gemcitabine (40 ng/ml, gemcitabine columns). MTT cytotoxicity assays were performed 144 h post treatment. Results of 3 independent experiments are shown. Statistically significant differences are indicated by an asterix (* for $P<0.05$, and ** for $P<0.005$).

D, EGFP transduction by a recombinant H-1PV into Panc-1 and Panc-1$^R$ cells. Cultures were treated (lower part) or not (upper part) with gemcitabine (40 ng/ml) and concomitantly infected with the viral vector (5 RU/cell). Cells expressing the transduced gene were detected by fluorescence microscopy at 48 h post infection. Representative fields are shown.

Figure 3:
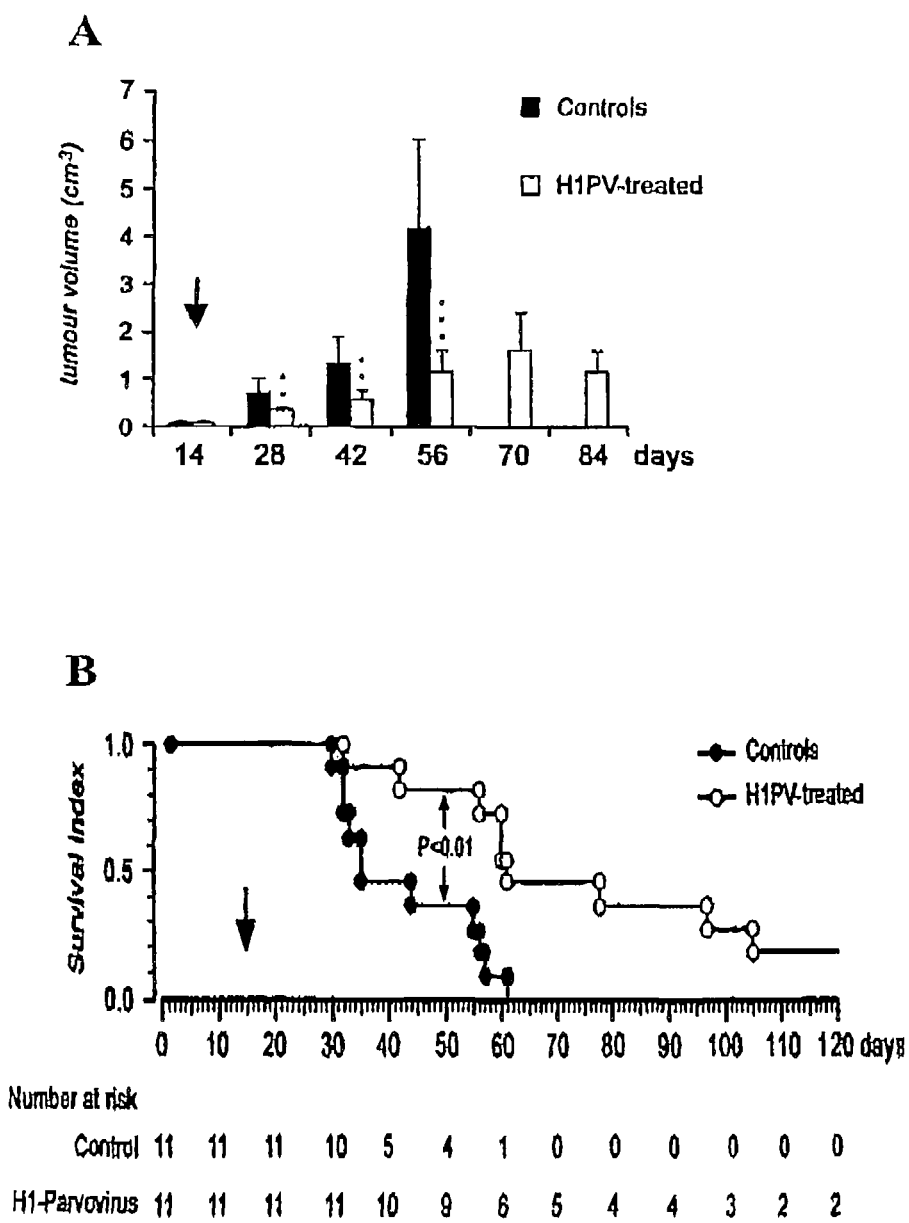
Figure 3:
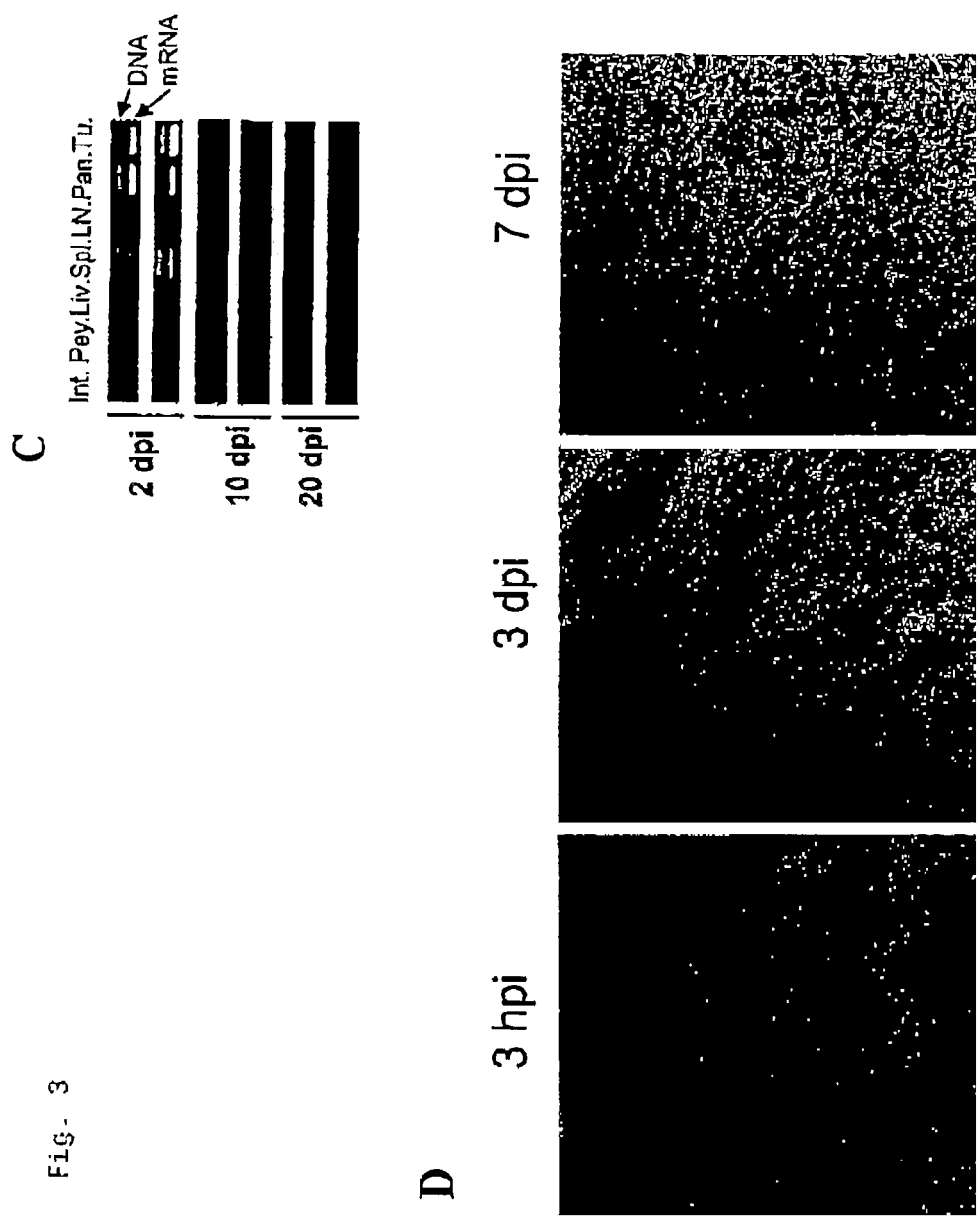

FIG. 3: Effect of H-1PV on a Rat Model of PDAC Formation

Rats (n=26) received an intrapancreatic injection of a cell suspension deriving from subcutaneous HA-RPC tumors, and the developing neoplasias were treated 2 weeks later by intratumoral inoculation of $1\times10^9$ RU H-1PV (n=16) or mock-treated (n=10).

A, Growth of H-1PV vs. mock-treated tumors. Tumor volumes were measured as a function of time by mCT scanning and are presented as means with SD bars.

B, Survival of H-1PV vs. mock-treated animals. Ten rats of each group were monitored over 120 days, at which time the experiment was terminated.

C, Distribution of H-1PV expression in tumor-bearing rats. Two rats in the H-1PV-treated group were sacrificed on days 2, 10 and 20 after infection, and their organs were processed for RT-PCR detection of viral transcripts. PCR products corresponding to viral DNA and precursor RNA (DNA/RNA) and mRNA are shown for the intestine (Int), Peyer's patches (Pey), liver (Liv), spleen (Spl), lymph nodes (LN), pancreas (Pan), and tumor (Tu).

D, immunohistochemical detection of H-1PV NS1 protein (arrows) in infected pancreatic tumors. Three PDAC-bearing rats were sacrificed at 3 h, 3 d and 7 d after intratumoral inoculation. Immunohistochemistry was performed on paraffin-embedded tumor sections (magnification 20×).

E, Characteristics of the rat tumor model: sensitivity to H-1PV infection and histology (a) Cells were cultured in 96-well plates and treated with increasing gemcitabine concentrations (4-4000 ng/ml), followed 24 h later by H-1PV infection (10 RU/cell). Cell survival was measured by performing MTT assays 72 h after infection, in comparison with mock-treated cultures (100%), and is inversely expressed as cell death rate.

(b) Paraffin-embedded tumor sections from normal rat pancreas and pancreatic tumor were subjected to hematoxylin-eosin staining; NP—normal pancreas, PDAC—pancreatic ductal carcinoma.

Figure 4:
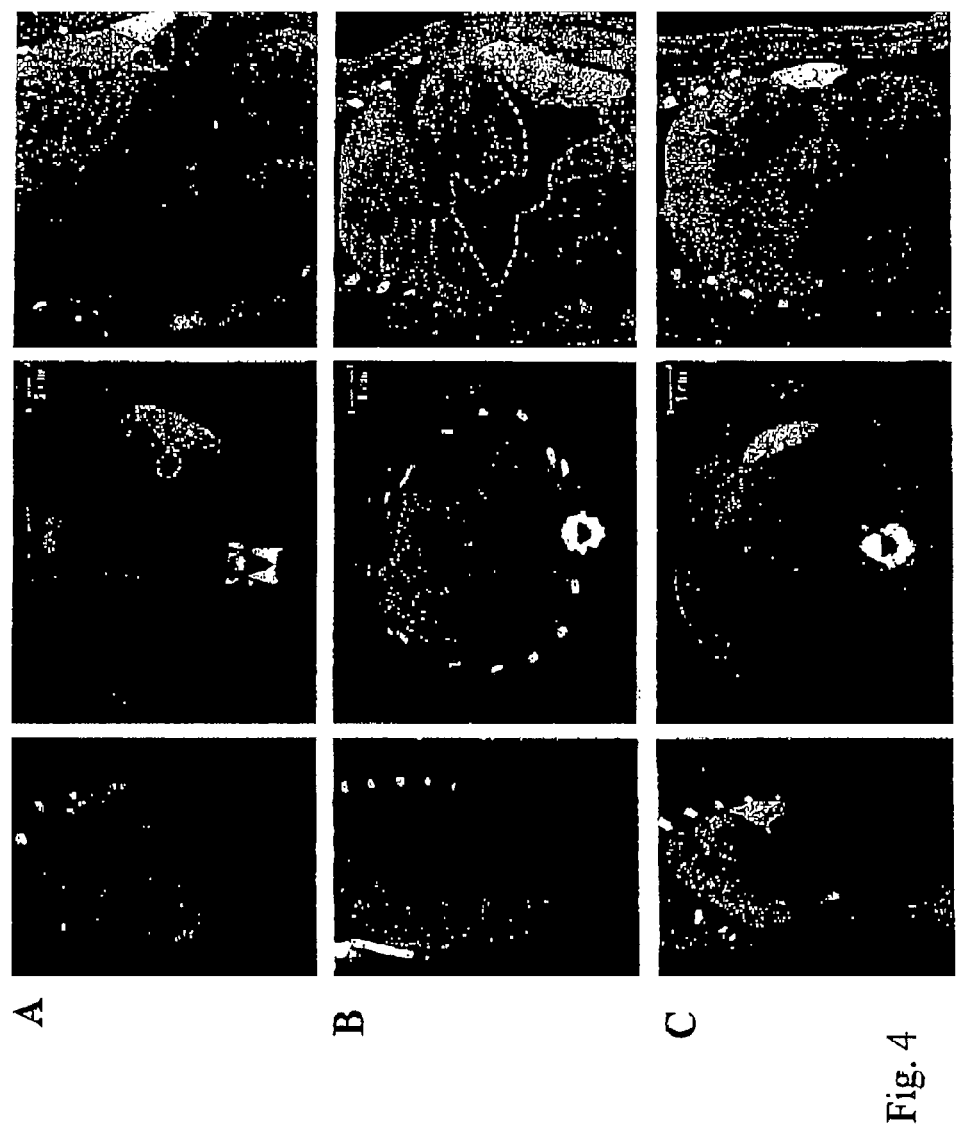

FIG. 4: mCT Imaging of Orthotopic Pancreatic Tumors

A, Abdominal CT scans of a rat at an early stage (2 weeks) after tumor initiation, showing a tumor approximately 5 mm in diameter (dotted lining) in the tail of the pancreas.

B, Evolution of PDAC in the absence of virotherapy, with a large primary tumor mass (dotted lines) and metastases in the lymph nodes and liver (arrows) 8 weeks post-initiation.

C, Regression of primary tumor and absence of metastases in a rat treated with H-1PV and examined 2 and 8 weeks post-initiation. Sagital, axial, and coronal mCT scan images were selected to illustrate the localization of primary tumors and metastases.

Figure 5:
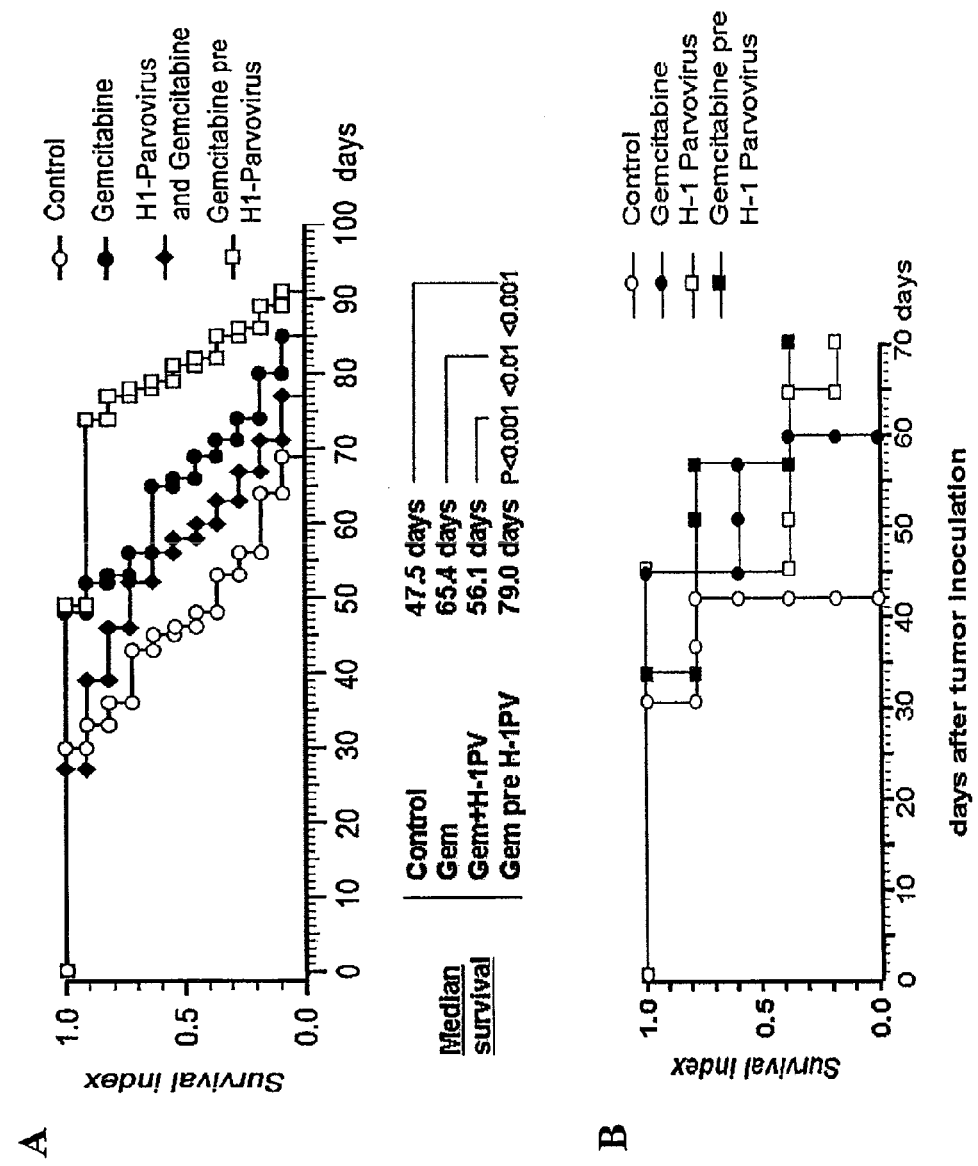

FIG. 5: Survival of Tumor-Bearing Animals After Combined Treatment with Gemcitabine and Parvovirus A, Rats bearing intrapancreatic tumors were divided into four groups (n=11) and treated with PBS (control), gemcitabine alone (gemcitabine), gemcitabine and virus simultaneously (H-1Parvovirus and gemcitabine), or gemcitabine first and H-1PV 14 days later (gemcitabine pre H-1Parvovirus). Animal survival was monitored over a period of 100 days and is presented as Kaplan-Meyer curves, with the median survival and P values indicated below.

B, Nude mice bearing subcutaneous BxPC-3 tumors were divided into four groups (n=5) and treated 21 days after tumor initiation with PBS (control), gemcitabine alone (gemcitabine), virus ($3\times10^8$ RU) alone (H-1Parvovirus), or gemcitabine first and H-1PV 7 days later (gemcitabine pre H-1Parvovirus).

Figure 6:
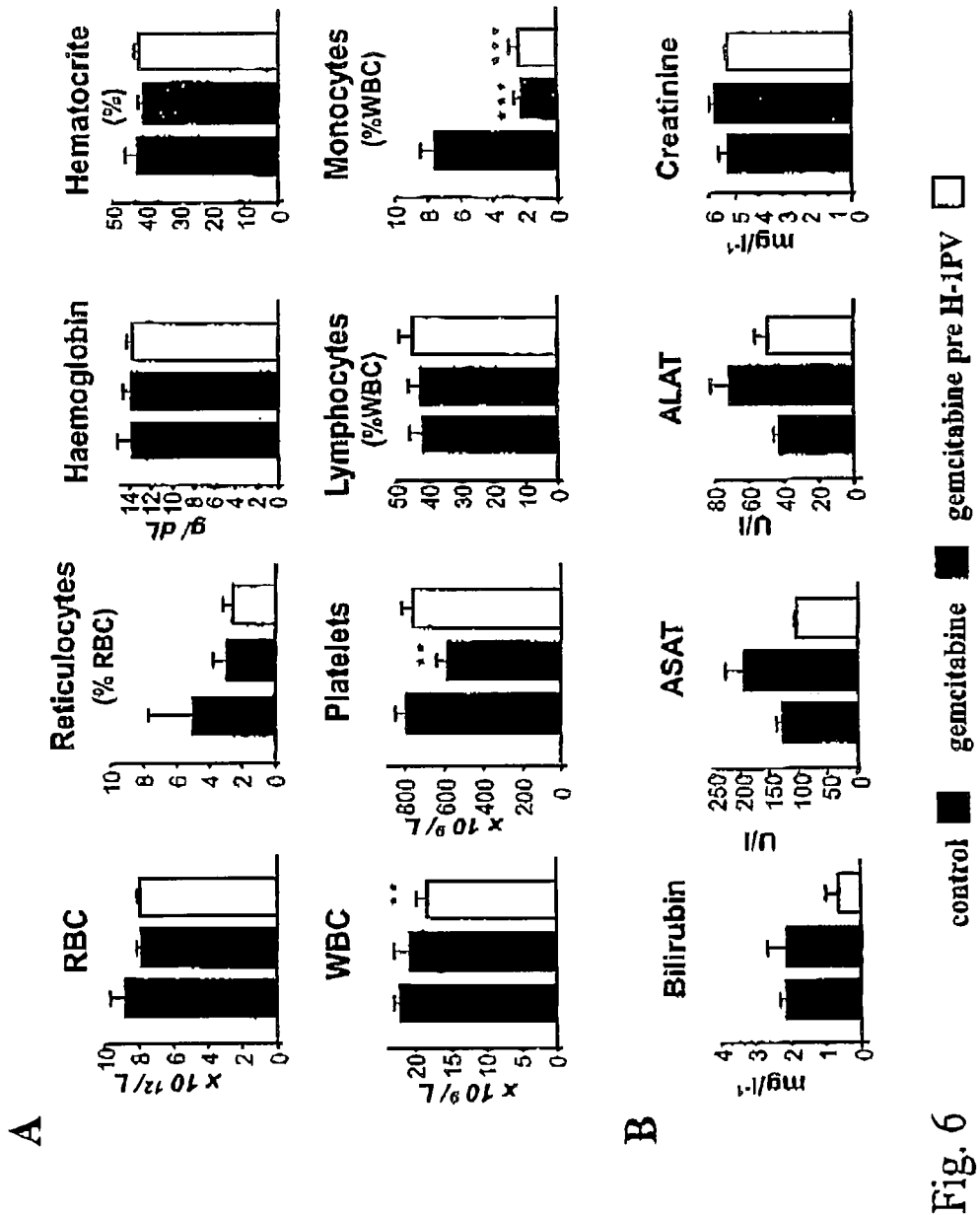

FIG. 6: Toxicological Assessment of the Gemcitabine and H-1PV Combination

Blood was collected from 3 PDAC-bearing rats each of the control, gemcitabine, and gemcitabine pre H-1PV groups (see FIG. 4A) 2 weeks after the last therapeutic treatment. Blood samples were analyzed for: (A) red blood cell (RBC), platelet, and white blood cell (WBC) counts and related parameters; (B) liver (aspartate amino transferase [ASAT], alanine amino transferase [ALAT]) and kidney (Creatinine) markers. The data shown are means with SD bars.

Figure 7:
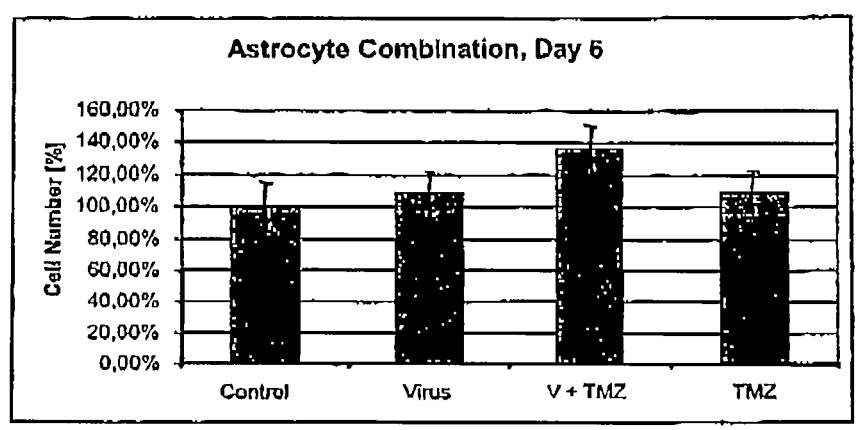

FIG. 7: Astrocytes after Treatment for 6 Days

The percentage of surviving human astrocytes (%) 6 days after treatment with H-1PV (Virus), combined treatment with H-1PV and TMZ (V+TMZ), and treatment with TMZ only (TMZ) is shown.

Figure 8A:
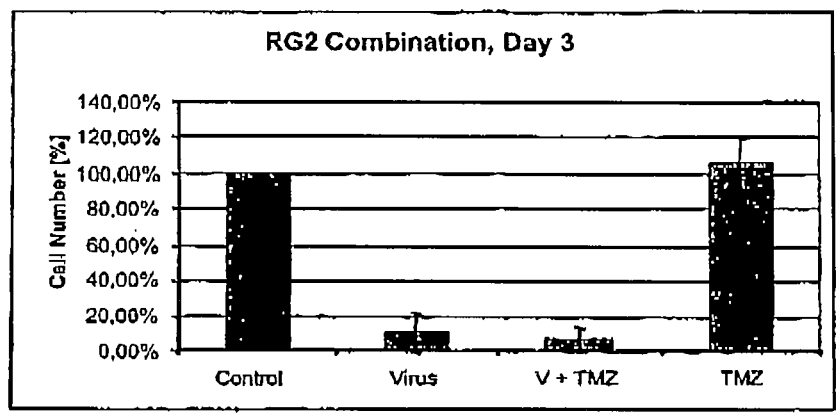
Figure 8B:
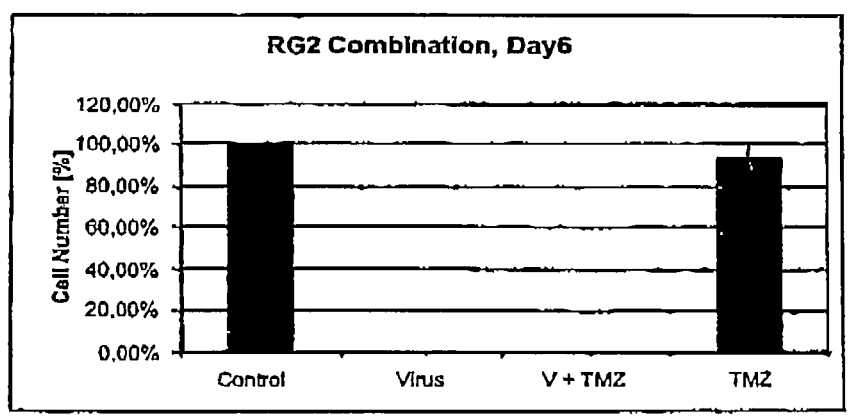

FIG. 8: RG2 Cells After Treatment for 3 Days and 6 Days, Respectively

The percentage of surviving RG2 cells [%] 3 days (A) and 6 days (B) after treatment with H-1PV (Virus), combined treatment with H-1PV and TMZ (V+TMZ), and treatment with TMZ only (TMZ) is shown.

Figure 9A:
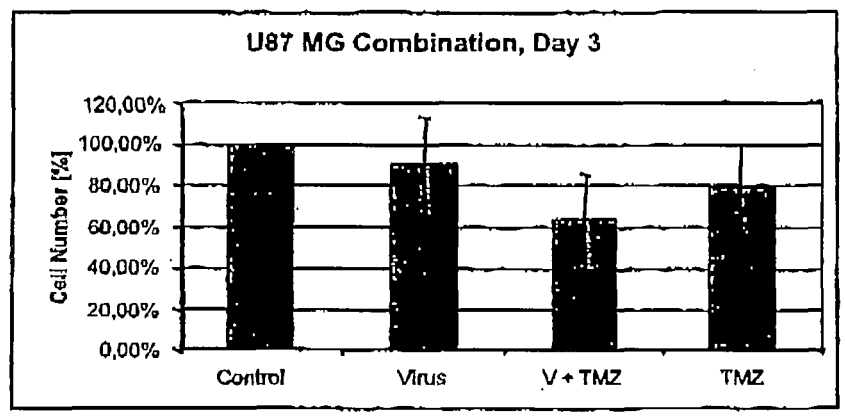
Figure 9B:
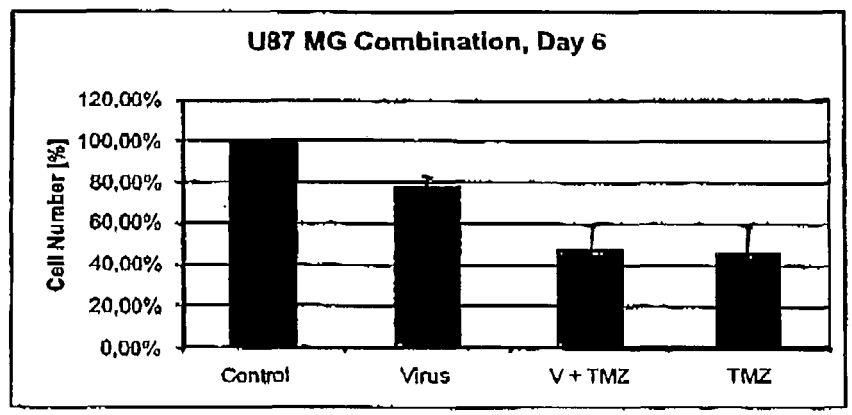

FIG. 9: U87MG Cells After Treatment for 3 Days and 6 Days, Respectively

The percentage of surviving U87MG cells [%] 3 days (A) and 6 days (B) after treatment with H-1PV (Virus), combined treatment with H-1PV and TMZ (V+TMZ), and treatment with TMZ only (TMZ) is shown.

Figure 10A:
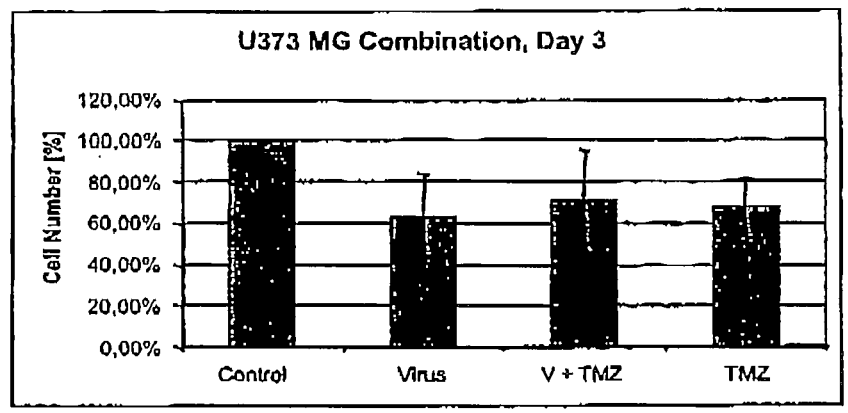
Figure 10B:
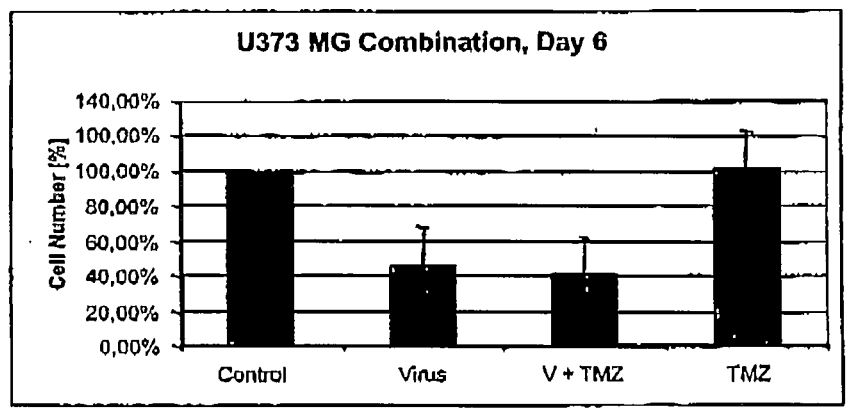

FIG. 10: U373MG Cells After Treatment for 3 Days and 6 Days, Respectively

The percentage of surviving U373MG cells [%] 3 days (A) and 6 days (B) after treatment with H-1PV (Virus), combined treatment with H-1PV and TMZ (V+TMZ), and treatment with TMZ only (TMZ) is shown.

Figure 11A:
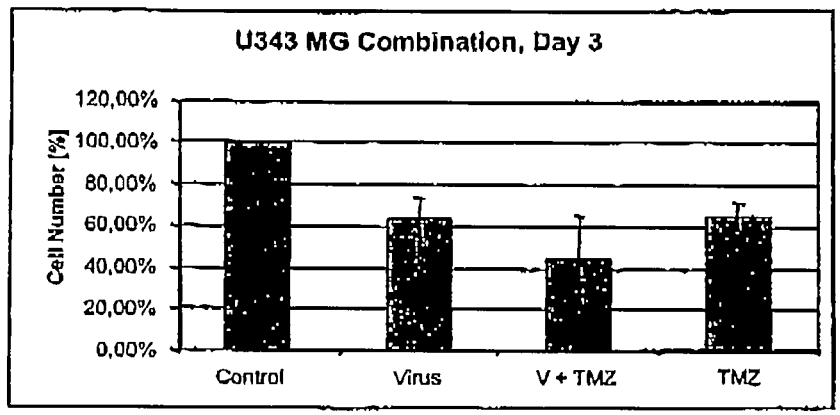
Figure 11B:
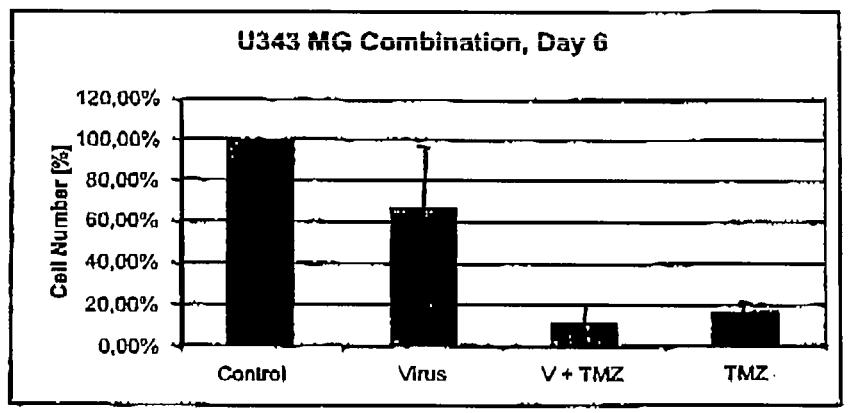

FIG. 11: U343MG Cells After Treatment for 3 Days and 6 Days, Respectively

The percentage of surviving U343MG cells [%] 3 days (A) and 6 days (B) after treatment with H-1PV (Virus), combined treatment with H-1PV and TMZ (V+TMZ), and treatment with TMZ only (TMZ) is shown.

Figure 12A:
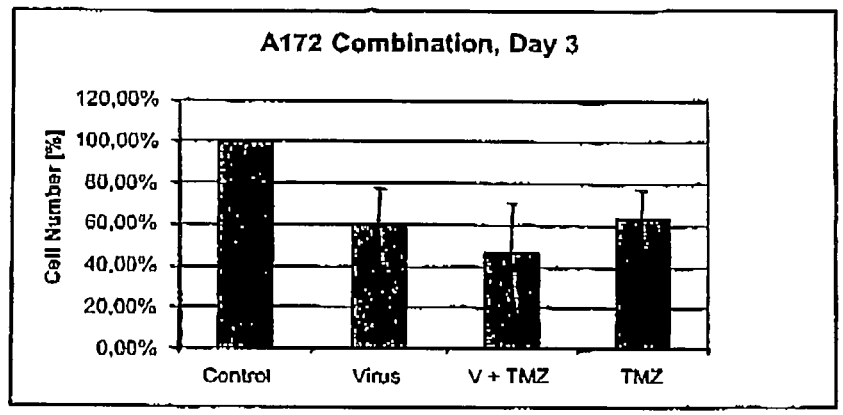
Figure 12B:
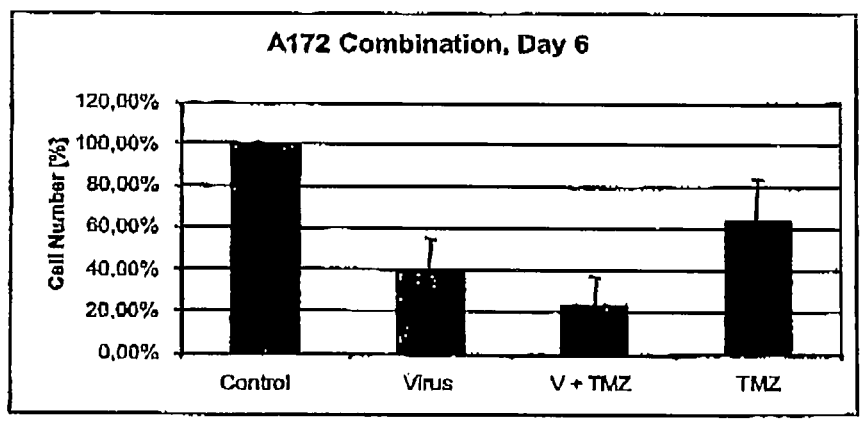

FIG. 12: A172 Cells After Treatment for 3 Days and 6 Days, Respectively

The percentage of surviving A172 cells [%] 3 days (A) and 6 days (B) after treatment with H-1PV (Virus), combined treatment with H-1PV and TMZ (V+TMZ), and treatment with TMZ only (TMZ) is shown.

Figure 13:
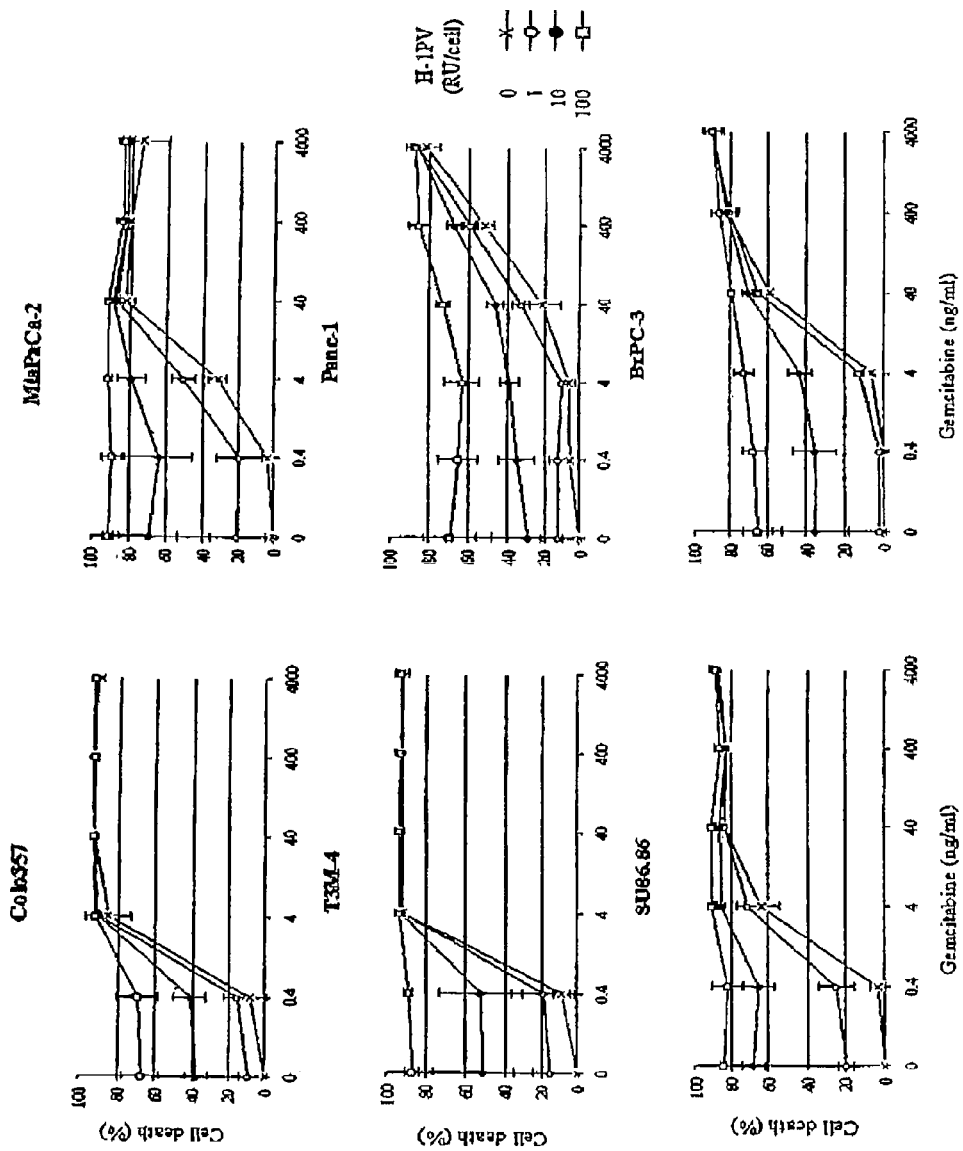

FIG. 13: Sensitivity of Human PDAC Cell Lines to the Toxic Effects of H-1PV Alone or Combined with Gemcitabine Colo357, T3M-4, SU86.86, MiaPaCa-2, Panc-1 and BxPC-3 cells were cultured at a densitiy of $2\times10^3$ cells per well in 96-well plates, and treated with gemcitabine (0.4-4000 ng/ml), followed 24 h later by H-1PV (1, 10 or 100 RU/cell). Survival was measured using MTT assays performed 72 h after infection, in comparison with mock-treated cultures (100%), and is inversely expressed as cell death rate. The data presented are means from 3 independent experiments carried out in quadruplicates.

Figure 14:
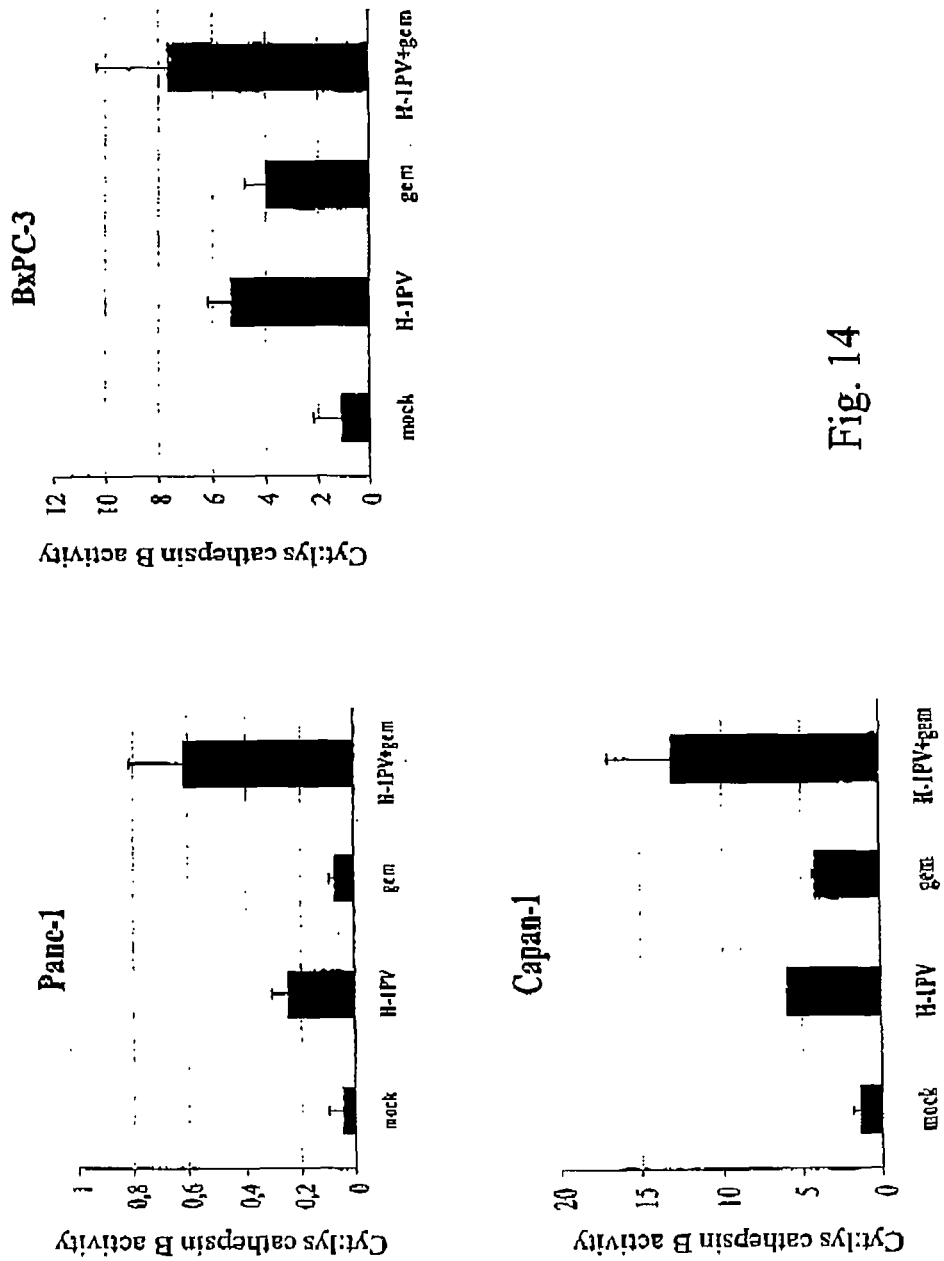

FIG. 14: Cathepsin B Activity in Treated PDAC Cell Lines

Panc-1, BxPC-3 and Capan-1 cells were treated with H-1PV (10 RU/cell) and gemcitabine (4 ng/ml), either alone or in combination, and processed for the determination of cytosolic and lysosomal cathepsin B activities. Cytosolic vs. lysosomal ratios are given and represent mean values with SD bars from 3 independent experiments.

Figure 15:
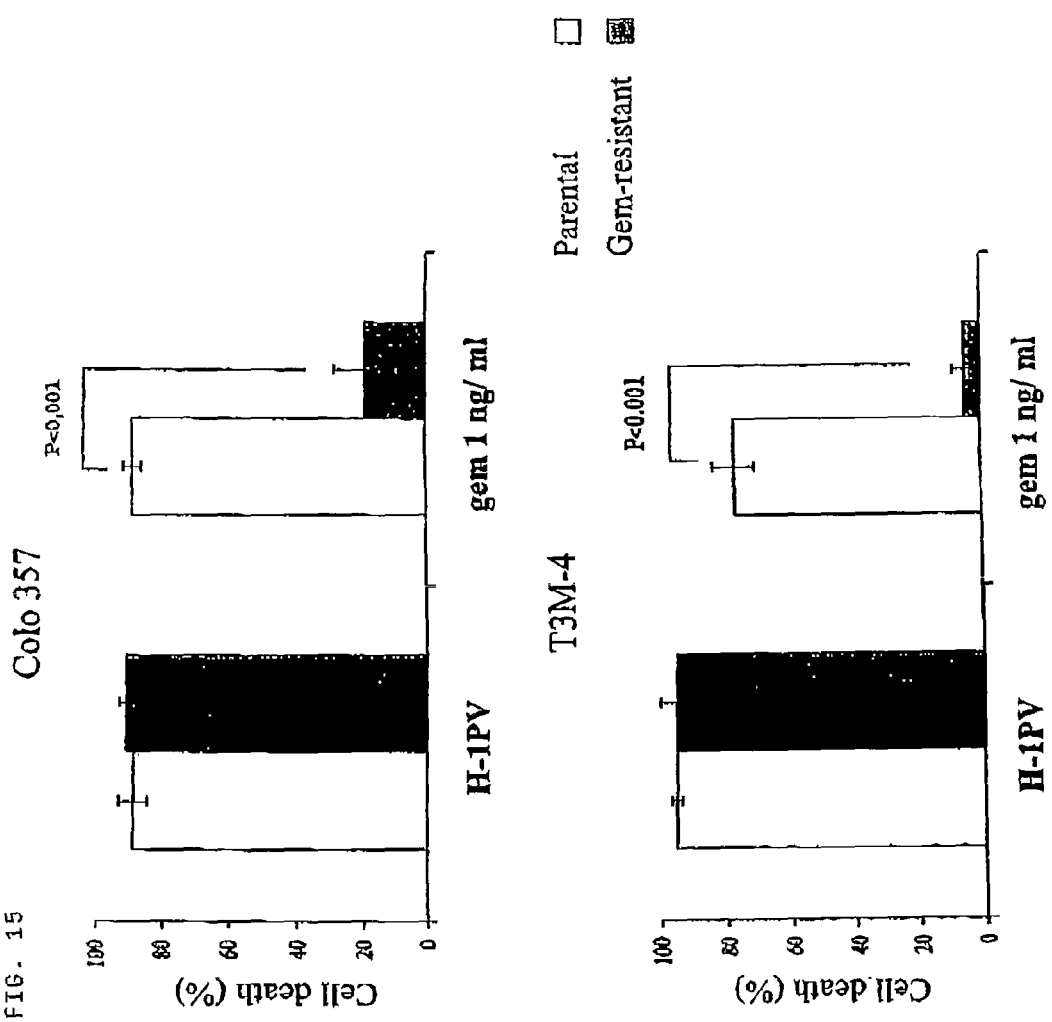

FIG. 15: Sensitivity of Gemcitabine-Resistant Colo357 and T3M-4 Cells to H-1PV-Induced Killing Cells selected for gemcitabine resistance after repeated drug exposure were treated 24 h after seeding with either gemcitabine (1 ng/ml) or H-1PV (10 RU/cell). For assessment of survival, MTT assays were performed 144 h after treatment. Data are expressed as percentages of cell death compared to mock-treated controls, and represent mean values with SD bars from 3 independent experiments carried out in quadruplicates.

The present invention provides a pharmaceutical composition containing a parvovirus and a chemotherapeutic agent, preferably (a) a parvovirus and (b) a chemotherapeutic agent as separate entities, e.g. in separate containers.

Preferably, in said pharmaceutical composition the parvovirus and the chemotherapeutic agent are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art (see for example, Fingl et al., The Pharmacological Basis of Therapeutics, Goodman and Gilman, eds. Macmillan Publishing Co., New York, pp. 1-46 ((1975)).

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical or intradermal administration. The route of administration, of course, depends on the kind of therapy and the kind of compounds contained in the pharmaceutical composition. A preferred route of administration is intravenous administration. The dosage regimen of the parvotherapeutic agent and the chemotherapeutic agent is readily determinable within the skill of the art, by the attending physician based an patient data, observations and other clinical factors, including for example the patient's size, body surface area, age, sex, the particular parvovirus, cell, chemotherapeutic agent etc. to be administered, the time and route of administration, the tumor type and characteristics, general health of the patient, and other drug thereapies to which the patient is being subjected.

If the parvotherapeutic agent(s) of the combination of agents according to the invention comprise infectious virus particles with the ability to penetrate through the blood-brain barrier, treatment can be performed or at least initiated by intravenous injection of the viral therapeutic agent, e.g., H1 virus. A preferred route of administration is intratumoral administration.

Since long-term intravenous treatment is susceptible to becoming inefficient as a result of the formation of neutralizing antibodies to the viral therapeutic agent, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the parvotherapeutic agent (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus or derived vectors can also be injected into the tumor by stereotactic surgical techniques or by neuronavigation targeting techniques.

Administration of the parvoviral agents or compositions can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvotherapeutic composition is from an implanted article constructed and arranged to dispense the parvotherapeutic agent to the desired cancer tissue. For example, wafers can be employed that have been impregnated with the parvotherapeutic composition, e.g., parvovirus H1, wherein the wafer is attached to the edges of the resection cavity at the conclusion of surgical tumor removal. Multiple wafers can be employed in such therapeutic intervention. Cells that actively produce the parvotherapeutic agent, e.g., parvovirus H1, or H1 vectors, can be injected into the tumor, or into the tumoral cavity after tumor removal.

The combined therapy according to the invention is useful for the therapeutic treatment of cancer, in particular brain tumors and pancreatic cancer, preferably pancreatic ductal adenocarcinoma (PDAC), and can significantly improve the prognosis of said diseases. Parvovirus H1 infection effects killing of tumor cells but does not barm normal cells and such infection can, for example, be carried out by intracerebral use of a suitable parvovirus, e.g., parvovirus H1, or a related virus or vectors based on such viruses, to effect tumor-specific therapy without adverse neurological or other side effects.

The present invention also relates to the use of a (a) a parvovirus and (b) a chemotherapeutic agent for the preparation of a pharmaceutical composition for the treatment of cancer wherein, preferably, (a) and (b) are sequentially (or separately) administered.

In one preferred embodiment of the present invention, the combination of agents is utilized in the treatment of (a) brain tumors such as glioma, medulloblastoma and meningioma or (b) pancreatic cancer. Preferred gliomas are malignant human glioblastomas.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

In another preferred embodiment of the present invention, the parvovirus of the composition includes parvovirus H1 (H1PV) or a related parvovirus such as LuIII, Mouse minute virus (MMV), Mouse parvovirus (MPV), Rat minute virus (RMV), Rat parvovirus (RPV) or Rat virus (RV).

Patients treatable by the combination of agents according to the invention include humans as well as non-human animals. Examples of the latter include, without limitation, animals such as cows, sheep, pigs, horses, dogs, and cats.

Chemotherapeutic agents useful for the purposes of the present invention include all chemical compounds that are effective in inhibiting tumor growth. The administration of chemotherapeutic agents can be accomplished in a variety of ways (see above) including systemically by the parenteral and enteral routes. Preferably, the parvovirus and the chemotherapeutic agent are administered as separate compounds.

In a further preferred embodiment, the parvovirus is administered after the chemotherapeutic agent. The preferred period of time between administration of the chemotherapeutic agent and the parvovirus is from 14 to 35 days.

Examples of suitable chemotherapeutic agents include alkylating agents, for example, nitrogen mustards, ethyleneimine compounds and alkyl sulphonates; antimetabolites, for example, folic acid, purine or pyrimidine antagonists, mitotic inhibitors, for example, vinca alkaloids and derivatives of podophyllotoxin; cytotoxic antibiotics; compounds that damage or interfere with DNA expression; and growth factor receptor antagonists.

Particular examples of chemotherapeutic agents suitable for the combined therapy include cisplatin, dacarbazine (DTIC), dactinomycin, mechlorethamine (nitrogen mustard), streptozocin, cyclophosphamide, carmustine (BNCU), lomustine (CCNU), doxorubicin (adriamycin), daunorubicin, procarbazine, mitomycin, cytrarabine, etoposide, methoothrexate, 5-fluorouracil, vinblastine, vincristine, bleomycin, paclitoaxel (taxol), docetaxel (taxotere), aldesleukin, asparginase, busulfan, carboplatin, cladribine, dacarbazine, floxuridine, fludarabine, hydroxyurea, ifosfamide, leuprolide, megestrol, melphalan, mercaptopurine, plicamycin, mitotane, pegaspargase, pentostatin, pipobraman, plicamycin, streptozocin, tamoxifen, teniposide, testolactone, thioguanine, thiotepea, uracil mustard, vinorelbine, chlorambucil and combinations thereof. Particularly preferred chemotherapeutic agents are Gemcitabine and Temozolomide.

Finally, the present invention also relates to the use of parvovirus H1 (H1PV) or a related rodent parvovirus, e.g., LuIII, Mouse minute virus (MMV), Mouse parvovirus (MPV), Rat minute virus (RMV), Rat parvovirus (RPV) or Rat virus (RV), for the preparation of a pharmaceutical composition for the treatment of pancreatic cancer. A preferred use is the treatment of a drug-resistant cancer, e.g., pancreatic cancer that is resistant to gemcitabine.

The below examples explain the invention in more detail.

EXAMPLE 1

Materials and Methods (A) Cell Culture and Treatment

The human pancreatic carcinoma cell lines and metastatic (Colo357, T3M-4 and SU86.86) tumors were obtained from ATCC (Manassas, Va.) and grown in RPMI 1640 (MiaPaCa-2, BxPC-3 and Capan-1) or DMEM (Panc-1) media supplemented with 10% fetal calf serum (FCS). Resistant cells were generated through multiple passages of cells with increasing doses of gemcitabine starting from a concentration of 0.0004 µg/ml for 2 hours and extended to 0.004 µg/ml for 24 hours.

The SV40—transformed newborn human kidney cells 293T and NBK cells (ATCC) were cultured in DMEM supplemented with 10% FCS. The cancer cell line HA-RPC developed from a chemically induced pancreatic ductal adenocarcinoma in Lewis rats was grown in DMEM with 10% FCS.[13] All culture media were supplemented with Penicillin (100 µg/ml) and Streptomycin (100 U/ml) and cells were kept at 37° C. in a 5% $CO_2$ atmosphere. Gemcitabine (Gemzar®, purchased from Lilly, Indianapolis, Ind., USA) was applied at the concentrations indicated in Legends to Figures.

For cytotoxicity assessment, cells were seeded in 96-well plates at a density of $2 \times 10^3$ cells per well and treated as indicated in the Figure Legends. Cell viability was determined by the colorimetric MTT (3-(4,5-dimethylthiazolyl-2)-2,5-diphenyltetrazolium bromide) assay, as recommended by the manufacturer (Sigma, Deisenhofen, Germany).

(B) Cell Viability

Cells plated in 96-well dishes and treated as indicated in the legends to the figures, were assessed for their viability by using colorimetric MTT (3-(4,5-dimethylthiazolyl-2)-2,5-diphenyltetrazolium bromide) assay. For clonogenicity assay cells were seeded at a density of 250 (Panc-1) or 800 (BxPC-3 and Capan-1) per 6 $cm^2$ dish, treated as indicated and further incubated for 14 days. After aspiration of the medium cell colonies were stained with Crystal Violet, washed with tap water and counted under the microscope. The surviving fractions (SF) were determined by the formula: SF=average number of colonies/[cells plated×(PE/100)], where PE is the plating efficiency of the respective cells in the absence of treatment.

(C) Microscopy

Cultures were examined using a Leica inverted microscope at a magnification of ×40. Image capture was performed using a Leica DFC350 FX camera (Leica Microsystems, Cambridge) and the Leica FireCam software for Macintosh. EGFP fluorescence was measured using a Leica DMRBE fluorescent microscope (Leica, Bensheim, Germany) and the analySIS software (Olympus, Germany).

(D) Virus Production and Detection

Wild type H-1 virus was produced by infecting NBK cells, purified by Iodixanol gradient centrifugation and dialyzed against Ringer solution. H-1PVEGFP recombinant virus was produced by cotransfecting 293T cells with the recombinant vector DNA and a helper plasmid expressing the viral capsid genes in trans.[14] Virus titers are determined as previously described and expressed as replication center-forming units (cfu). Briefly, serial dilutions of purified viruses were applied to NBK cells. At 48 hours post infection, infected cultures were blotted onto filters and replication centers were detected by hybridization, using a virus DNA-specific radioactive probe.[10]

For the analysis of virus transcription in the organs of treated animals or PDAC cell cultures, total RNA was extracted from samples of collected tissues or cell pellets, with Trizol Reagent (Invitrogen, Karlsruhe, Germany), according to manufacturer's instructions. RNA was reverse transcribed into cDNA and quantified using previously detailed RT-PCR protocol.[15] H-1PV transcripts were detected in the form of 512 and 415 bp PCR fragments, depending on the excision of the small intron, using pair of primers: [SEQ ID NO: 1] 5'-TCAATGCGCTCAC-CATCTCTG-3' (forward) and [SEQ ID NO: 2} 5'-TCGTAG-GCTTCGTCGTGTTCT-3' (reverse). The primers specific for hENT and dCK mRNAs were as follows: hENT-[SEQ ID NO: 3] 5'-AAAGGAGAGGAGCCAAGAGC-3' (forward) and [SEQ ID NO: 4] 5'-GGCCCAACCAGTCAAAGATA-3' (reverse); dCK-[SEQ ID NO: 5] 5'-CCCGCATCAA-GAAAATCTCC-3' (forward) and [SEQ, ID NO: 6] 5'-TC-CATCCAGTCATGCCAGTC-3' (reverse). The primers used for detecting the expression of human β-actin, and MDR, MRP1 and MRP2 genes have been previously described. [16]

(E) Animal Studies (i) Anaesthesia.

All surgical and imaging procedures were performed under gaseous anaesthesia with 3% isoflurane (Aerrane®, Baxter, Maurepas, France) in pure oxygen and a concomitant intramuscular injection of 2-3 mg/kg of xylazine hydrochloride (Rompun®, Bayer, Leverkusen, Germany) as analgesia for surgery.

(ii) Tumor Model.

Male Lewis rats (Janvier, Le Genest Saint Isle, France) weighing 180-200 g were used for pancreatic carcinoma implantation. $5.10^6$ HA-RPC cells were injected in the pancreatic parenchyma. Tumor progression is confined to the pancreatic tail for the first 3 weeks after implantation, leading to lymph node invasion during the $4^{th}$ week. Liver metastases appear at weeks 5-6 and death with lung metastasis occurs within weeks 6-9.[17] Animals were kept under conventional conditions (temperature 22±2° C., relative humidity 55±10%, dark-light rhythm of 12 hr) with unrestricted access to a balanced pellet diet and water. Animal experiments were performed according to the French and European Community directives for animal care (number 86/609/EEC of Nov. 24, 1986).

Gemcitabine was applied through an intraperitoneal injection (100 mg/kg). H-1PV was inoculated intratumorally (i.t.). Blood samples were taken from animal tail vein 2 weeks after the last therapeutic treatment. Toxicological markers were assayed in Strasbourg University Hospital using automated clinical laboratory analysis (Biochemical multiparametric device Biochime ADVIA 160, Siemens, Cergy Pontoise, France).

(iii) Image Acquisition and Reconstruction.

Images were obtained on an Imtek microCT scanner (microCAT-II, Imtek Inc., Knowville, Tenn.) using a 80 kVp X-ray voltage and 500 μA anode current. Respiratory-gated acquisition was used to avoid changes in abdominal organ position and consequent delineation blurring. Fenestra® LC and Fenestra® VC contrast agents (Alerion Biomedical Inc., San Diego, Calif.) devoted to liver and persistent vascular contrast, respectively were concomitantly injected intraperitoneally 9 h prior imaging. Image data were acquired and reconstructed using Imtek licensed software (Cobra version 4.1-4, Exxim computing corporation, Knoxville, Tenn.). 3D images were visualized using Amira software (Amira Advanced Visualization, Data analysis, and Geometry Reconstruction v.3.1, San Diego, Calif.). Tumors or metastases, which appeared as black defects within the contrasted liver or pancreatic lobe, were measured three-dimensionally using the Amira 3D data set.

(F) Immunohistochemistry

Paraffin-embedded tumor sections were dewaxed with xylene and rehydrated through graded alcohol solutions. Endogenous peroxidase activity was quenched with 0.3% hydrogen peroxide in methanol. To block the non-specific binding, slides were treated with non-immune normal rabbit serum (Dako, Zurich, Switzerland) for 1 h. After overnight incubation (4° C.) with the H-1PV NS1 protein-specific 3D9 antibody (1:50) (kind gift from Dr. Nathalie Salomé, DKFZ, Heidelberg, Germany), slides were washed and treated with rabbit anti-mouse horseradish peroxidise-labelled secondary antibody (1:200; Sigma), developed using the Dako Envision+™ System (Dako) and counterstained with Mayer's hematoxylin.

(G) Statistical Analysis (i) In Vitro Studies.

Means and standard deviations (SD) were calculated from triplicate in vitro experiments. To determine whether H-1PV and gemcitabine interact synergistically in vitro, we performed an isobolographic analysis based on the data derived from MTT assays, as already described for other combinations of chemo- and virotherapy [22]. The 50% and 75% effective concentration (EC) values ($EC_{50}$ and $EC_{75}$) for gemcitabine and H-1PV were determined empirically on the basis of a range of concentrations (0.4 to 4000 ng/ml) and MOIs (1, 10, 100 RU/cell), respectively. The isobologram was created from the data obtained for the combination of the two agents. Combination (CI) and sensitization (SI) indices were calculated using the following equations: $CI=(D_{H1.c}/D_{H1.a})+(D_{G.c}/D_{G.a})+(D_{H1.c}*D_{G.c}/D_{H1.a}*D_{G.a})$; $SI_{H-1PV}=D_{H1.a}/D_{H1.c}$; $SI_{gem}=D_{G.a}/D_{G.c}$, where $D_{H1.c}$, $D_{H1.a}$, $D_{G.c}$ and $D_{G.a}$ are the respective $EC_{50/75}$ doses of H-1PV or gemcitabine, alone (H1.a, G.a) or in combination (H1.c, G.c). CI=1 represents the conservation isobologram and indicates additive effects. CI values below 1 indicate higher than the expected additive effect (synergy).

(ii) In Vivo Studies.

Mean and standard deviations from triplicate in vitro experiments were calculated. Difference in tumour volume, determined in vivo through mCT-scan size measurements, was tested using a one-way analysis of variance followed by a parametric Student's unpaired t test as Bartlett's test indicated homogeneity of variance. A difference between the values was considered significant when P<0.05. The survival curves were generated using the Kaplan-Meier method, and the differences between the curves were assessed by the log-rank test. A P-value <0.05 was considered to be statistically significant. Instat 2.00 Macintosh software (GraphPad Software, San Diego, Calif.) was used.

(H) Cell Fractionation and Protease Activity Measurements

Cathepsin B activity was determined in cytosolic and lysosomal fractions obtained from Panc-1 and BxPC-3 cells treated with gemcitabine alone (4 ng/ml), H-1PV alone (10 RU/cell) or both agents in combination. Cultures were collected in phosphate-buffered saline (PBS), pelleted by centrifugation, resuspended in hypotonic buffer (0.25 M sucrose, 50 mM HEPES-NaOH [pH 7.4], 1 mM EDTA) and homogenized in a cell cracker. Nuclei and heavy mitochondria were pelleted by centrifugation at 2500×g for 10 min at 4° C. An aliquot of the supernatant (post-nuclear suspension, PNS) was kept and used to determine enzyme latency. The light mitochondrial fraction (LMF) was obtained by PNS centrifugation at 17000×g for 20 min at 4° C. The supernatant was recovered as cytosolic extract, and the LMF pellet was resuspended in hypotonic buffer. Cytosolic and LMF fractions were each added to a reaction mixture consisting of 50 mM morpholineethanesulfonic acid (MES) (pH 6.0), 0.25 M sucrose, 1 mM EDTA, and 2 mM N-acetyl-L-cysteine. After 10 min incubation, the substrate Z-Arg-Arg-AMC (Calbiochem) was added (1 mM), and emission was monitored for 1 h on a Fluoroskan & FL luminometer (Thermolabsystem) at a wavelength of 455 nm after excitation at 360 nm.

(I) Isolation of Gemcitabine-Resistant Colo357 and T3M-4 Cells

Gemcitabine-resistant Colo357 and T3M-4 cells were isolated through five selection cycles, each involving the treatment of cells for 48 h with the gemcitabine $EC_{50}$ determined for the respective parental line (1.2 ng/ml for T3M-4 and 1.5 ng/ml for Colo357). Drug sensitivity of parental and resistant cells was assessed in both MTT and clonogenic survival assays.

EXAMPLE 2

Figure 1:
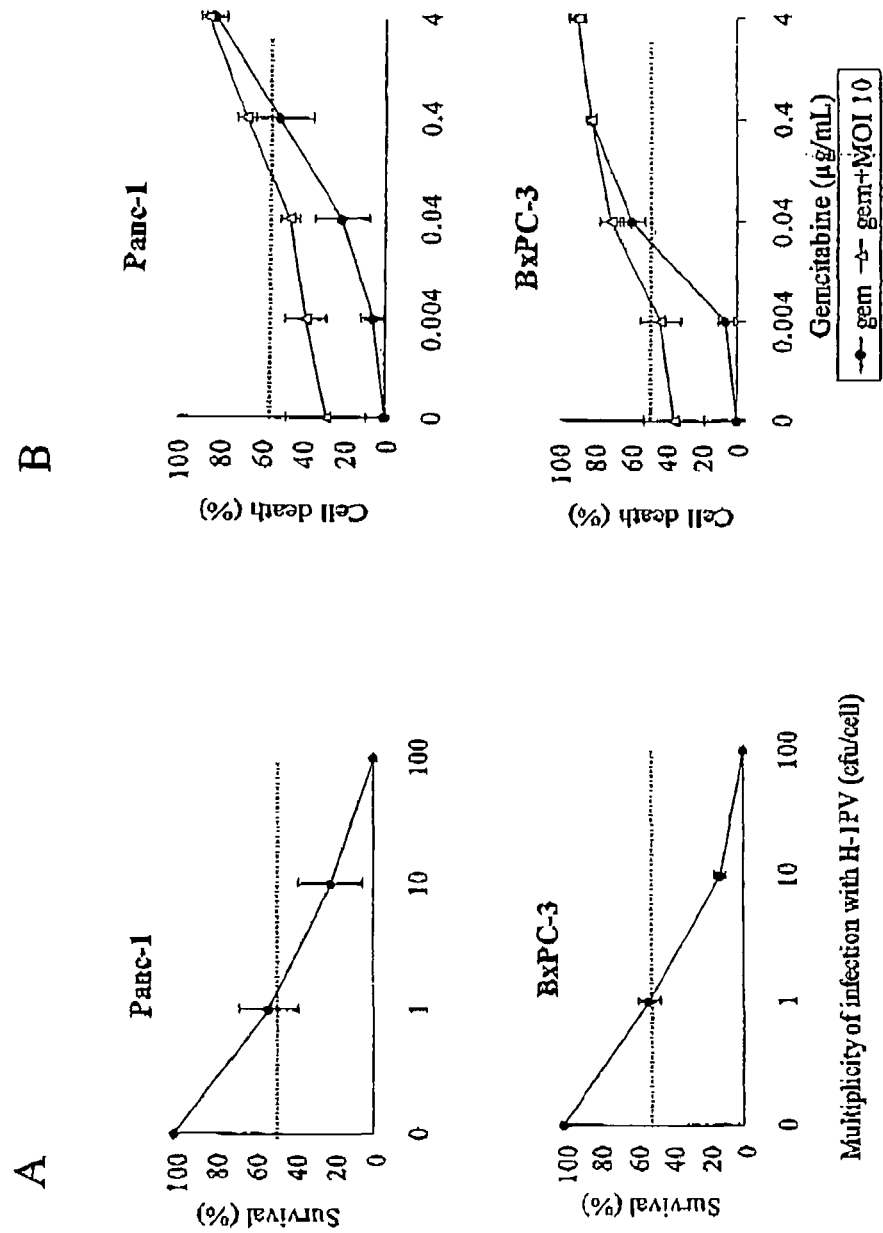
FIG. 1: Sensitivity of Human PDAC Cell Lines to the Toxic Effects of H-1PV Alone or Combined with Gemcitabine (A) Residual colony-forming ability of Panc-1 and BxPC-3 cells after H-1PV infection at indicated MOIs. Colonies were counted after Crystal Violet staining, and survival is presented as percentage of mock-treated cells.

H-1PV, Both Alone and in Cooperation with Gemcitabine, Kills Cultured Human Pancreatic Cancer Cells Causing a Release of Active Cathepsin B in the Cytoplasm Six human PDAC cell lines, Colo357, T3M-4, SU86.86, MiaPaCa-2, Panc-1 and BxPC-3, were tested for their sensitivity to H-1PV and gemcitabine toxicity (Table 1, FIG. 1 and FIG. 13). MiaPaCa-2, SU86.86 and T3M-4 were found to be hypersensitive to virus-induced killing, while Colo357, SU86.86 and T3M-4 were most susceptible to gemcitabine. Importantly, the cell lines that showed stronger resistance to gemcitabine treatment (Panc-1, BxPC-3 and MiaPaCa-2) were sensitive to H-1PV.

Table 1

TABLE 1

Combined toxic effects of H-1PV and gemcitabine on human PDAC cells

| Cell line | $EC_{50/75}$ | H-1PV MOI | | gemcitabine (ng/ml) | CI | $SI_{H-1PV}$ | $SI_{Gem}$ |
|---|---|---|---|---|---|---|---|
| BxPC3 | $EC_{50}$ mono. | 30 | | 25 | | | |
| | $EC_{50}$ comb. 1 | 1 | + | 20 | 0.86 | 30 | 1.3 |
| | $EC_{50}$ comb. 2 | 10 | + | 7.0 | 0.71 | 3 | 3.6 |
| Colo357 | $EC_{50}$ mono. | 35 | | 1.5 | | | |
| | $EC_{50}$ comb. 1 | 1 | + | 1.3 | 0.92 | 35 | 1.2 |
| | $EC_{50}$ comb. 2 | 10 | + | 0.6 | 0.80 | 3.5 | 2.5 |
| MiaPaCa-2* | $EC_{75}$ mono. | 20 | | 30 | | | |
| | | (4) | | (9) | | | |
| | $EC_{75}$ comb. 1 | 1 | + | 18 | 0.68 | 20 | 1.7 |
| | $EC_{75}$ comb. 2 | 10 | + | 2.0 | 0.60 | 2 | 15.0 |
| Panc-1 | $EC_{50}$ mono. | 35 | | 400 | | | |
| | $EC_{50}$ comb. 1 | 1 | + | 200 | 0.54 | 35 | 2.0 |
| | $EC_{50}$ comb. 2 | 10 | + | 60 | 0.48 | 3.5 | 6.7 |
| SU86.86* | $EC_{75}$ mono. | 30 | | 17 | | | |
| | | (4) | | (2.5) | | | |
| | $EC_{75}$ comb. 1 | 1 | + | 8.0 | 0.52 | 30 | 2.1 |
| | $EC_{75}$ comb. 2 | 10 | + | 1.3 | 0.44 | 3 | 13.1 |
| T3M-4* | $EC_{75}$ mono. | 45 | | 2.5 | | | |
| | | (10) | | (1.2) | | | |
| | $EC_{75}$ comb. 1 | 1 | + | 2.4 | 1.00 | 45 | 1.0 |
| | $EC_{75}$ comb. 2 | 10 | + | 1.5 | 0.96 | 4.5 | 1.7 |

Cultures were seeded in 96-well plates at $2 \times 10^3$ cells/well, treated with gemcitabine (0.4-4000 ng/ml) and infected 24 hrs later with H-1PV at different MOIs (1, 10, 100 RU/cell). Cytototoxicity was assessed using MTT assays 72 hrs after infection. $EC_{50}$ values for single (mono) and combined (comb) treatments were calculated from isobolograms that were created using MTT measurements obtained at different MOIs (H-1PV) and concentrations (gemcitabine).
The combination index (CI) and sensitization index (SI) were determined as described in Materials and Methods.
*Due to the hypersensitivity of indicated cell lines to H-1PV killing, $EC_{75}$ values were used for statistical analyses. The $EC_{50}$ values for H-1PV and gemcitabine monotherapy are given in brackets.

As indicated in Table 1, the cytotoxic effect of the combined therapy was in most cases synergistic (CI<1), in particular in MiaPaCa-2, Panc-1 and SU86.86 cells. The effective virus dose could be reduced by a factor ($SI_{H-1PV}$) of up to 35-fold in the presence of gemcitabine doses ranging from 1.3 ng/ml (Colo357, combination 1) to 200 ng/ml (Panc-1, combination 1). Conversely, the effective drug concentration required to inhibit cell proliferation was reduced by a factor ($SI_{Gem}$) of up to 15-fold when the cells were infected with H-1PV (MiaPaCa-2, combination 2). The ability of all cell lines to form colonies over a 2-week period was also efficiently inhibited by both H-1PV (data not shown).

Moreover, it was determined whether the subcellular distribution of cathepsin B activity in PDAC-derived lines was also altered after the above treatments. This was tested using three human PDAC cell lines. As shown in FIG. 14, the cytosolic accumulation of functional cathepsin B was significantly enhanced by the H-1PV/gemcitabine combination, strongly suggesting that this mechanism might participate in the observed cumulative toxicity.

EXAMPLE 3

H-1PV Can Kill Both Gemcitabine-Sensitive and -Resistant Cells with Similar Efficiency Since the development of resistance to gemcitabine is a major drawback of long-term treatment of PDAC patients with this drug, the cytopathic effects of H-1PV on gemcitabine-resistant cell variants derived from two of the above-mentioned lines (Panc-1 and BxPC-3) that differed in their natural sensitivity to gemcitabine was tested (Table 1). Resistant ($^R$) populations were isolated by sequentially treating cells with increasing doses of the drug. Resistant variants were distinguishable from the respective parental cell lines by their slower growth and stable phenotypic changes, such as enhanced expression of the MDR and MRP1/2 drug-export markers (FIG. 2A). As the levels of import (hENT) and activation (dCK) markers remained unchanged or slightly reduced (FIG. 2A), it seems that the resistant phenotype was mostly due to more intensive gemcitabine export. The drug-resistant variants remained sensitive to H-1PV infection (FIGS. 2B and 2C, H-1PV column), while they resisted an extended incubation with gemcitabine (40 ng/ml for 144 h) that was toxic for the original lines (FIG. 2C, gemcitabine column). A slight but significant increase in H-1PV-induced killing was even observed in BxPC-3$^R$ vs. BxPC-3 cells. This suggests that H-1PV might be used as a second-line treatment of PDAC to circumvent acquired resistance to gemcitabine. Furthermore, the gemcitabine-resistant phenotype was found to correlate with reduced interference of toxic drug doses with progression of the parvoviral life-cycle. Indeed, marker-protein EGFP expression, driven by a recombinant parvoviral vector, persisted in Panc-1$^R$ cells even after they were exposed to a gemcitabine dose abolishing EGFP transduction in parental cells (FIG. 2D). Thus, it can be concluded that chemoresistant tumor cell variants remain targets of H-1PV even under conditions in which gemcitabine therapy is continued. Efficient virus killing was similarly observed after infection of gemcitabine-resistant Colo357 and T3M-4 cells selected using short-term treatment with high gemcitabine doses (FIG. 15). In agreement with these data, the resistant and parental Colo357 and T3M-4 lines had a similar capacity for virus replication (data not shown).

Altogether, in vitro experiments suggest that H-1PV may improve the therapeutic effect of gemcitabine, both by reinforcing the overall killing of drug-sensitive cells and by eradicating chemoresistant variants emerging at late stages of drug treatment.

EXAMPLE 4

H-1PV Induces Partial to Full Suppression of Orthotopic Pancreatic Tumors, Thereby Prolonging the Animals' Survival To mimic the clinical situation more closely, a syngeneic rat model of orthotopically implanted PDAC was used to evaluate the anticancer activity of H-1PV. Since the rat is the natural host of H-1PV, the system is also suitable for toxicological assessment of this oncolytic agent—another prerequisite to its clinical application. The rat PDAC cells used in the model (HA-RPC) were first tested in vitro for their susceptibility to H-1PV infection, and proved to have the same range of sensitivity to virus and gemcitabine toxicity as the above-mentioned human cells (FIG. 3E(a)).

H-1PV was then administered in vivo through a single intratumoral injection 2 weeks after implantation of HA-RPC cells into the pancreas. Tumor size (measured by mCT scanning and macroscopic inspection after death), animal survival, and virus distribution were determined. Virotherapy caused a delay in tumor growth (FIG. 3A) and as illustrated in FIG. 3B, rats in the virus-treated group survived significantly longer than the mock-treated controls, with 20% remaining disease-free for 16 weeks (until the end of the experiment). Importantly, H-1PV was expressed selectively in tumors, as opposed to normal tissues. To confirm this, we tested visceral organs for the presence of virus transcripts (by RT-PCR). As shown in FIG. 3C, an initial burst of virus expression shortly after infection in the tumor and the surrounding pancreatic tissue was observed. In agreement with previous observations in other models, H-1PV was also distributed to lymphoid organs [15]. From day 10 on, virus expression faded, most likely due to the appearance of virus-neutralizing antibodies reducing virus spread [18]. However, it persisted in the tumor for up to 20 days post-inoculation. In addition, the intratumoral dissemination of the virus could be confirmed by immunohistochemical analysis (FIG. 3D).

It has to be noted that in some cases, complete disappearance of pre-existing tumors was observed on mCT scans (FIG. 4, compare A and C). Besides local expansion of the primary tumor, lympho- and hematogenous metastases affecting respectively the visceral lymph nodes of the upper abdominal cavity and liver play a major role in PDAC mortality. As expected, mCT monitoring of uninfected rats revealed metastatic invasion of local pancreatic, pyloric, and hepatic lymph nodes and of the liver (FIG. 4B, arrows). Inoculation of the primary tumor with H-1PV at an early stage (corresponding to the FIG. 4A images) resulted in 45% suppression of distant metastases as well as of the primary tumor, at a later time (FIG. 4C). Interestingly, the spreading of metastatic disease to the liver in this model correlated with late virus expression in the organ (FIG. 3C), suggesting that H-1PV can actively control tumor invasion.

EXAMPLE 5

H-1PV Suppresses PDAC Tumors Escaping Gemcitabine Treatment

It was investigated whether H-1PV can enhance the therapeutic effect of gemcitabine in vivo, as observed in vitro (Table 1, FIG. 13). To mimic a clinically plausible scenario, PDAC-bearing rats were first treated with gemcitabine and 2 weeks later the tumor was inoculated intraoperatively with H-1PV. As depicted in FIG. 5A (gemcitabine pre H-1PV), this led to significantly prolonged survival of the animals, as compared to mock treatment (control) or monotherapy with the chemotherapeutic (gemcitabine). When both agents were applied simultaneously (H-1PV and gemcitabine), H-1PV failed to improve the therapeutic effect of gemcitabine. This is probably due to negative interference of the genotoxic drug with the parvoviral life cycle (see also FIG. 2D).

In order to test the effectiveness of gemcitabine and H-1PV in a different in vivo model using human cells, BxPC-3 tumors were induced in nude mice and treated with a similar regimen as the one used in rats (FIG. 5B). All animals receiving therapy had a prolonged survival compared to controls. Combined treatment (gemcitabine pre H-1PV, n=5) and H-1PV monotherapy (n=5) achieved the highest level of anti-tumor protection, with one animal from each of these groups remaining tumor-free up to 70 days after the beginning of the experiment. At this time, 40% of the animals from the combined treatment group were still alive, while all control mice had to be sacrificed by 40 days post-implantation.

Altogether, these data confirm that gemcitabine provides transient protection against PDAC, and that subsequent administration of H-1PV can extend the animals' survival. Furthermore, toxicological assessment of the therapeutic regimens was carried out in the rat model, indicating that the blood-borne markers of bone marrow activity were largely unaffected (FIG. 6A), apart from a drop in reticulocyte and monocyte levels due to gemcitabine treatment. Clinical reports prompted us to monitor the liver and kidney functions as well (FIG. 6B). The bilirubin, ASAT, and ALAT levels were elevated in the untreated and gemcitabine-treated groups, revealing a low-grade lytic process in the livers of PDAC-bearing rats. Additional parvovirotherapy restored these markers to levels within the physiological range. Creatinine levels remained stable, demonstrating unaffected kidney clearance. In conclusion, the detected blood parameter anomalies were fully attributable to gemcitabine treatment and were not aggravated by subsequent H-1PV administration.

EXAMPLE 6

H1-PV Infection Can Improve the Therapeutic Effect of Temozolomide on Glioblastoma Cells in Vitro Initially, the rates of survival of the cell lines used in the study were determined using MTT assays in order to check whether these cell lines are sensitive for H-1PV infection and Temozolomide (TMZ) treatment. In addition, the rates of survival after combined treatment with H-1PV and TMZ were determined. Cells were infected with an MOI and 5 pfU/cell and treated with 25 µM TMZ assuming that these concentrations show clear effects but do not result in complete lysis of the cells. The graphs of FIGS. 7-11 depict the results after 3 and 6 days, respectively. After 3 days of treatment distinct effects can already be observed. After 6 days the experiments were terminated since control cells were already confluent. In addition, after 6 days further analyses could not be carried out due to the very low rate of survival (depending on the particular cell line).

As a control, human astrocytes were (a) infected with H-1PV, (b) treated with TMZ or (c) subjected to combined treatment. As shown in FIG. 8, none of these treatments shows any effect on the astrocytes.

As shown in FIG. 8, RG2 cells are very sensitive for H1-PV infection, 3 days after infection about 90% of the cells are already lysed. The same result is obtained with the combined treatment (H-1PV+TMZ). After 6 days, all cells are killed. In addition, the results show that the cells are not sensitive to TMZ treatment.

As shown in FIG. 9, 3 days after H-1PV infection only about 10% of U87MG cells are lysed, after treatment with TMZ alone, about 20% of the cells were killed. The combined treatment (H1-PV+TMZ) showed a stronger cytolytic effect, about 40% of the cells were killed. However, 6 days after treatment, this effect was no longer present and the rate of survival of cells subjected to combined treatment resembled the rate of survival of cells treated with TMZ only (TMZ).

As shown in FIG. 10, treatment with TMZ showed no cytotoxic effect on U373 cells (6 days after treatment). Upon infection with H-1PV about 60% of cells were lysed after 6 days. The same result was obtained with the combined treatment (Hi-PV+TMZ).

FIG. 11 shows the results obtained with U343 cells which are very sensitive to TMZ treatment. After 6 days, more than 80% of the cells are killed. 3 days after treatment, combination of H-1PV and TMZ showed a stronger cytapathic effect compared to the single treatments. However, after 6 days, this effect is less pronounced and the percentage of surviving cells after combined treatment approaches the percentage of surviving cells after treatment with TMZ alone.

As shown in FIG. 12, the combined treatment with H-1PV and TMZ gives an enhanced cytopathic effect in comparison to the treatments with H-1PV alone and TMZ alone, respectively.

In summary, it could be demonstrated that established human and animal (rat) glioblastoma cell lines as well short term cell lines derived from human glioblastomas are very sensitive to virus mediated cell death. This result could be confirmed in the present study using an established rat cell line, TG2, and various human glioblastoma cell lines, U87MG, U373MG, U343MG and A172 (obtainable from the Deutsches Krebsforschungszentrum (DKFZ), Heidelberg, Germany) which were lytically infected with H-1PV. A low dose of 5 infectious particles per cell was sufficient for obtaining a distinct cyopathic effect after 72 h. In addition, it could be shown that H-1PV infected human astrocytes did not lyse. Treatment of normal astrocytes, RG2 cells and U373 cells with 25 µM Temozolomide (TMZ) did not result in cell death. The cells were resistant even if much higher doses were administered.

The further human cell lines were sensitive to TMZ treatment. Combined treatment with H-1PV and TMZ showed that the oncolytic effect of the virus was not impaired by TMZ treatment. On the other hand, the virus had no inhibiting effect on TMZ treatment. It can be expected that—similar to the results reported for the combined treatment of pancreatic cancer with H-1PV and gemcitabine—not only additive but even synergistic effects can be achieved in vivo by the combined treatment with H-1PV and TMZ.

LIST OF REFERENCES

1. Jemal A, Thomas A, Murray T, et al. Cancer statistics, 2002. *Cancer J Clin* 2002; 52:23-47.
2. Pisani P, Parkin D M, Bray F I, et al. Estimates of the worldwide mortality from 25 cancers in 1990. *Int J Cancer* 1999; 83:18-29.
3. Finlayson E, Birkmeyer J D. Effects of hospital volume on life expectancy after selected cancer operations in older adults: a decision analysis. *J Am Coll Surg* 2003; 196:410-17.
4. Burris H A 3rd, Moore M J, Andersen J, et al. Improvements in survival and clinical benefit with gemcitabine as first-line therapy for patients with advanced pancreas cancer: a randomized trial. *J Clin Oncol* 1997; 15:2403-13.
5. Giovannetti E, Mey V, Nannizzi. S, et al. Pharmacogenetics of anticancer drug sensitivity in pancreatic cancer. *Mol Cancer Ther* 2006; 5:1387-95.
6. Hecht J R, Bedford R, Abbruzzese J L, et al. A phase I/II trial of intratumoral endoscopic ultrasound injection of ONYX-015 with intravenous gemcitabine in unresectable pancreatic carcinoma. *Clin Cancer Res* 2003; 9:555-61.
7. Rommelaere J, Cornelis J. Antineoplastic activity of parvoviruses. *J Virol Methods* 1991; 33:233-51.
8. Cotmore S F, Tattersall P. The autonomously replicating parvoviruses of vertebrates. *Adv Virus Res* 1987; 33:91-174.
9. Haag A, Menten P, Van Damme J, et al. Highly efficient transduction and expression of cytokine genes in human tumor cells by means of autonomous parvovirus vectors; generation of antitumor responses in recipient mice. *Hum Gene Ther* 2000; 11:597-609.
10. Russell S J, Brandenburger A, Flemming C L, et al. Transformation-dependent expression of interleukin genes delivered by a recombinant parvovirus. *J Virol* 1992; 66:2821-8.
11. Olijslagers S, Dege A Y, Dinsart C, et al. Potentiation of a recombinant oncolytic parvovirus by expression of Apoptin. *Cancer Gene Ther* 2001; 8:958-65.
12. Di Piazza M, Mader C, Geletneky K, et al. Cytosolic activation of cathepsins mediates parvovirus H-1-induced killing of cisplatin and TRAIL-resistant glioma cells. *J Virol* 2007; 81:4186-98.
13. Evrard S, Keller P, Hajri A, et al. Experimental pancreatic cancer in the rat treated by photodynamic therapy. *Br J Surg* 1994; 81:1185-89.
14. Wrzesinski C, Tesfay L, Salome N, et al. Chimeric and pseudotyped parvoviruses minimize the contamination of recombinant stocks with replication-competent viruses and identify a DNA sequence that restricts parvovirus H-1 in mouse cells. *J Virol* 2003; 77:3851-8.
15. Giese N A, Raykov Z, DeMartino L, et al. Suppression of metastatic hemangiosarcoma by a parvovirus MVMp vector transducing the IP-10 chemokine into immunocompetent mice. *Cancer Gene Ther* 2002; 9:432-42.
16. Schaarschmidt T, Merkord J, Adam U, et al. Expression of multidrug resistance proteins in rat and human chronic pancreatitis. *Pancreas* 2004; 28:45-52.
17. Mutter D, Hajri A, Tassetti V, et al. Increased tumor growth and spread after laparoscopy vs laparotomy: influence of tumor manipulation in a rat model. *Surg Endosc* 1999; 13:365-70.
18. Raykov Z, Balboni G, Aprahamian M, et al. Carrier cell-mediated delivery of oncolytic parvoviruses for targeting metastases. *Int J Cancer* 2004; 109:742-9.
19. Harrop R, Carroll M W. Viral vectors for cancer immunotherapy. *Front Biosci* 2006; 11:804-17.
20. Raykov Z, Grekova S, Galabov A S, et al. Combined oncolytic and vaccination activities of parvovirus H-1 in a metastatic tumor model. *Oncol Rep* 2007; 17:1493-9.
21. Plate J M, Plate A E, Shott S, et al. Effect of gemcitabine on immune cells in subjects with adenocarcinoma of the pancreas. *Cancer Immunol Immunother* 2005; 54:915-25.
22. Nowak A K, Robinson B W, Lake R A. Gemcitabine exerts a selective effect on the humoral immune response: implications for combination chemo-immunotherapy. *Cancer Res* 2002; 62:2353-8.
22. 18. Bennett J J, Adusumilli P, Petrowsky H., et al. Up-regulation of GADD34 mediates the synergistic anticancer activity of mitomycin C and a gamma134.5 deleted oncolytic herpes virus (G207). *FASEB J* 2004; 18:1001-3.

The invention claimed is:

1. A method for the treatment of cancer comprising administering to a patient in need thereof an effective amount of (a) parvovirus and (b) a chemotherapeutic agent,
    wherein said parvovirus (a) is H1 (HIPV) or a related rodent parvovirus selected from the group consisting of LuIII, Mouse minute virus (MMV), Mouse parvovirus (MPV), Rat minute virus (RMV), Rat parvovirus (RPV) or Rat virus (RV),
    wherein the parvovirus (a) is administered after the chemotherapeutic agent (b),
    wherein the chemotherapeutic agent (b) is gemcitabine or Temozolomide, and
    wherein said cancer is a brain tumor or pancreatic cancer.

2. The method according to claim 1, wherein said pancreatic cancer is pancreatic ductal adenocarcinoma (PDAC).

3. The method according to claim 1, wherein said brain tumor is a glioma, medulloblastoma or meningioma.

4. The method according to claim 3, wherein said glioma is a malignant human glioblastoma.

5. The method according to claim 1, wherein said parvovirus is administered by intratumoral administration.

6. A method for the treatment of pancreatic cancer comprising administering to a patient in need thereof a parvovirus H1 (HIPV) or a related rodent parvovirus selected from the group consisting of LuIII, Mouse minute virus (MMV), Mouse parvovirus (MPV), Rat minute virus (RMV), Rat parvovirus (RPV) or Rat virus (RV).

7. The method according to claim 6, wherein said pancreatic cancer is a drug-resistant cancer.

8. The method according to claim 7, wherein the drug is gemcitabine.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: artificial sequence
<220> FEATURE:
<223> OTHER INFORMATION: primer

<400> SEQUENCE: 1
tcaatgcgct caccatctct g         21

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
tcgtaggctt cgtcgtgttc t         21

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
aaaggagagg agccaagagc          20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
ggcccaacca gtcaaagata          20

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
cccgcatcaa gaaaatctcc          20

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
tccatccagt catgccagtc          20